United States Patent
Amelon et al.

(10) Patent No.: US 11,633,260 B1
(45) Date of Patent: Apr. 25, 2023

(54) POSITIONING INDIVIDUAL THREE-DIMENSIONAL MODEL TEETH BASED ON TWO-DIMENSIONAL IMAGES

(71) Applicant: SDC U.S. SmilePay SPV, Nashville, TN (US)

(72) Inventors: Ryan Amelon, Nashville, TN (US); Jared Lafer, Nashville, TN (US); Ramsey Jones, Nashville, TN (US); Tim Wucher, Windhoek (NA); Jordan Katzman, Nashville, TN (US); Martin Chobanyan, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 17/831,587

(22) Filed: Jun. 3, 2022

(51) Int. Cl.
| | |
|---|---|
| *A61C 7/00* | (2006.01) |
| *G06T 5/20* | (2006.01) |
| *G06T 7/00* | (2017.01) |
| *G06T 7/70* | (2017.01) |
| *G06T 7/136* | (2017.01) |

(Continued)

(52) U.S. Cl.
CPC ............... *A61C 7/002* (2013.01); *G06T 5/20* (2013.01); *G06T 7/0014* (2013.01); *G06T 7/136* (2017.01); *G06T 7/70* (2017.01); *G06T 17/20* (2013.01); *G16H 30/40* (2018.01); *A61C 2007/004* (2013.01); *G06T 2207/20081* (2013.01); *G06T 2207/30036* (2013.01); *G06T 2210/41* (2013.01)

(58) Field of Classification Search
CPC ..... A61C 7/002; A61C 2007/004; G06T 5/20; G06T 7/0014; G06T 7/136; G06T 7/70; G06T 17/20; G06T 2207/20081; G06T 2207/30036; G06T 2207/41; G16H 30/40
See application file for complete search history.

(56) References Cited

U.S. PATENT DOCUMENTS

| | | |
|---|---|---|
| 10,076,389 B2 | 9/2018 | Wu et al. |
| 10,166,088 B2 | 1/2019 | Sachdeva et al. |
| 10,945,813 B2 | 3/2021 | Li et al. |

(Continued)

FOREIGN PATENT DOCUMENTS

WO    WO-2021245480 A1 * 12/2021

OTHER PUBLICATIONS

US 11,182,981 B2, 11/2021, Long et al. (withdrawn)

*Primary Examiner* — Ping Y Hsieh
*Assistant Examiner* — Jose M Torres
(74) *Attorney, Agent, or Firm* — Foley & Lardner LLP

(57) ABSTRACT

Systems and methods for generating a 3D model of a dentition are disclosed herein. A method includes generating a first 3D model of a dentition including a plurality of model teeth. The method includes receiving at least one digital representation comprising patient teeth. The method includes determining a virtual camera parameter. The virtual camera parameter corresponds with a camera used to capture the digital representation. The method includes comparing, based on the virtual camera parameter, a first position of a model tooth with a position of a corresponding patient tooth of the digital representation. The method includes moving the model tooth from the first position to a second position. The second position is based on the position of the corresponding patient tooth. The method includes generating a second 3D model comprising the model tooth of the first 3D model in the second position.

19 Claims, 11 Drawing Sheets

(51) Int. Cl.
*G16H 30/40* (2018.01)
*G06T 17/20* (2006.01)

(56) References Cited

U.S. PATENT DOCUMENTS

| | | | |
|---|---|---|---|
| 10,952,817 B1 | 3/2021 | Raslambekov | |
| 11,020,205 B2 | 6/2021 | Li et al. | |
| 11,026,767 B1 | 6/2021 | Raslambekov | |
| 11,033,361 B2 | 6/2021 | Tsai et al. | |
| 2016/0019364 A1* | 1/2016 | Badawi | A61C 7/002 |
| | | | 703/11 |
| 2017/0049311 A1* | 2/2017 | Borovinskih | G06T 7/0016 |
| 2017/0319293 A1 | 11/2017 | Fisker | |
| 2019/0239982 A1 | 8/2019 | Cinader, Jr. | |
| 2020/0000552 A1 | 1/2020 | Mednikov et al. | |
| 2020/0360109 A1* | 11/2020 | Gao | G06T 7/0012 |
| 2020/0390521 A1 | 12/2020 | Kopelman et al. | |
| 2020/0405447 A1 | 12/2020 | Salah et al. | |
| 2021/0045843 A1 | 2/2021 | Pokotilov et al. | |
| 2021/0074061 A1 | 3/2021 | Brown et al. | |
| 2021/0113302 A1 | 4/2021 | Boltunov et al. | |
| 2021/0186659 A1 | 6/2021 | Li et al. | |
| 2021/0244502 A1* | 8/2021 | Farkash | G06N 20/00 |
| 2021/0312220 A1 | 10/2021 | Borovinskih et al. | |
| 2022/0030162 A1* | 1/2022 | Cramer | A61C 9/0053 |
| 2022/0211466 A1* | 7/2022 | Raslambekov | A61C 7/002 |
| 2022/0222910 A1* | 7/2022 | Salah | G06V 10/17 |

* cited by examiner

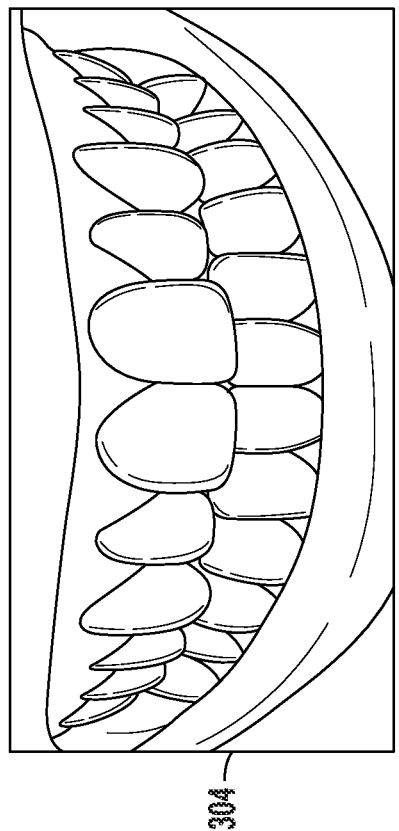
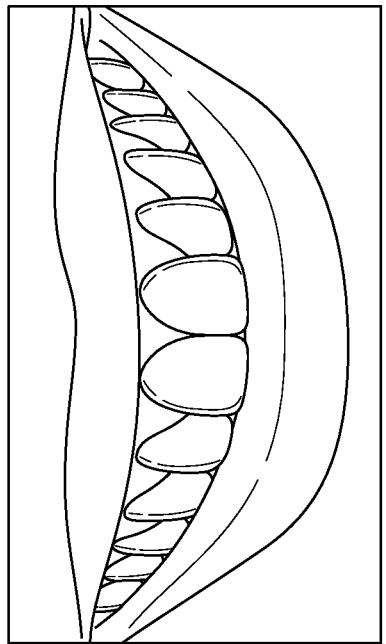
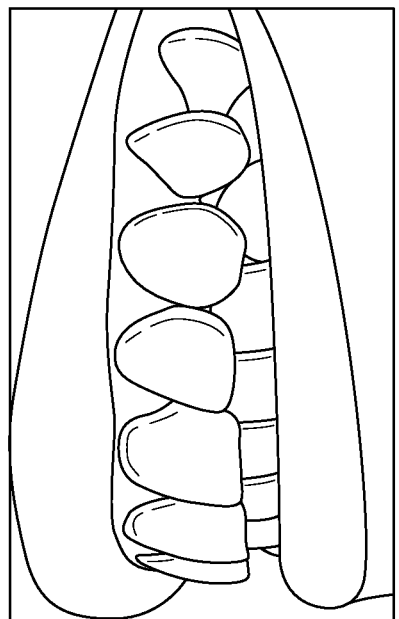
FIG. 3

POSITIONING INDIVIDUAL THREE-DIMENSIONAL MODEL TEETH BASED ON TWO-DIMENSIONAL IMAGES

TECHNICAL FIELD

The present disclosure relates generally to the field of dental imaging and treatment, and more specifically, to systems and methods for generating a digital dentition model.

BACKGROUND

Orthodontic treatment is often used to reposition a patient's teeth. Monitoring the patient's teeth during treatment ensures the teeth move as expected to a desired position. In-person appointments are inconvenient and time consuming, and specialized equipment for monitoring treatment can be expensive or difficult to correctly use.

SUMMARY

In one aspect, this disclosure is directed to a method. The method includes generating, by one or more processors, a first 3D model of a dentition. The dentition includes a plurality of model teeth. The method includes receiving, by the one or more processors, at least one digital representation comprising a plurality of patient teeth. The method includes determining, by the one or more processors, a virtual camera parameter associated with a virtual camera. The virtual camera parameter corresponds with a parameter of a camera used to capture the at least one digital representation. The method includes comparing, by the one or more processors based on the virtual camera parameter, a first position of a model tooth of the first 3D model with a position of a corresponding patient tooth of the at least one digital representation. The method includes moving, by the one or more processors, the model tooth of the first 3D model from the first position to a second position, wherein the second position is based on the positon of the corresponding patient tooth. The method includes generating, by the one or more processors, a second 3D model comprising the model tooth of the first 3D model in the second position.

In one aspect, this disclosure is directed to a system. The system includes a processor and a memory. The memory is coupled with the processor. The memory is configured to store instructions that, when executed by the processor, cause the processor to generate a first 3D model of a dentition. The dentition includes a plurality of model teeth. The instructions cause the processor to receive at least one digital representation comprising a plurality of patient teeth. The instructions cause the processor to determine a virtual camera parameter associated with a virtual camera. The virtual camera parameter corresponds with a parameter of a camera used to capture the at least one digital representation. The instructions cause the processor to compare, based on the virtual camera parameter, a first position of a model tooth of the first 3D model with a position of a corresponding patient tooth of the at least one digital representation. The instructions cause the processor to move the model tooth of the first 3D model from the first position to the second position. The second position is based on the position of the corresponding patient tooth. The instructions cause the processor to generate a second 3D model comprising the model tooth of the first 3D model in the second position.

In yet another aspect, this disclosure is directed to a non-transitory computer readable medium that stores instructions. The instructions, when executed by one or more processors, cause the one or more processors to generate a first 3D model of a dentition. The dentition includes a plurality of model teeth. The instructions cause the one or more processors to receive at least one digital representation comprising a plurality of patient teeth. The instructions cause the one or more processors to determine a virtual camera parameter associated with a virtual camera. The virtual camera parameter corresponds with a parameter of a camera used to capture the at least one digital representation. The instructions cause the one or more processors to compare, based on the virtual camera parameter, a first position of a model tooth of the first 3D model with a position of a corresponding patient tooth of the at least one digital representation. The instructions cause the one or more processors to move the model tooth of the first 3D model from the first position to a second position. The second position is based on the actual relative 3D position of the corresponding patient tooth as reflected in the images. The instructions cause the one or more processors to generate a second 3D model comprising the model tooth of the first 3D model in the second position.

Various other embodiments and aspects of the disclosure will become apparent based on the drawings and detailed description of the following disclosure.

BRIEF DESCRIPTION OF THE DRAWINGS

FIG. 3 shows a digital representation, according to various illustrative embodiments.

DETAILED DESCRIPTION

Figure 1:
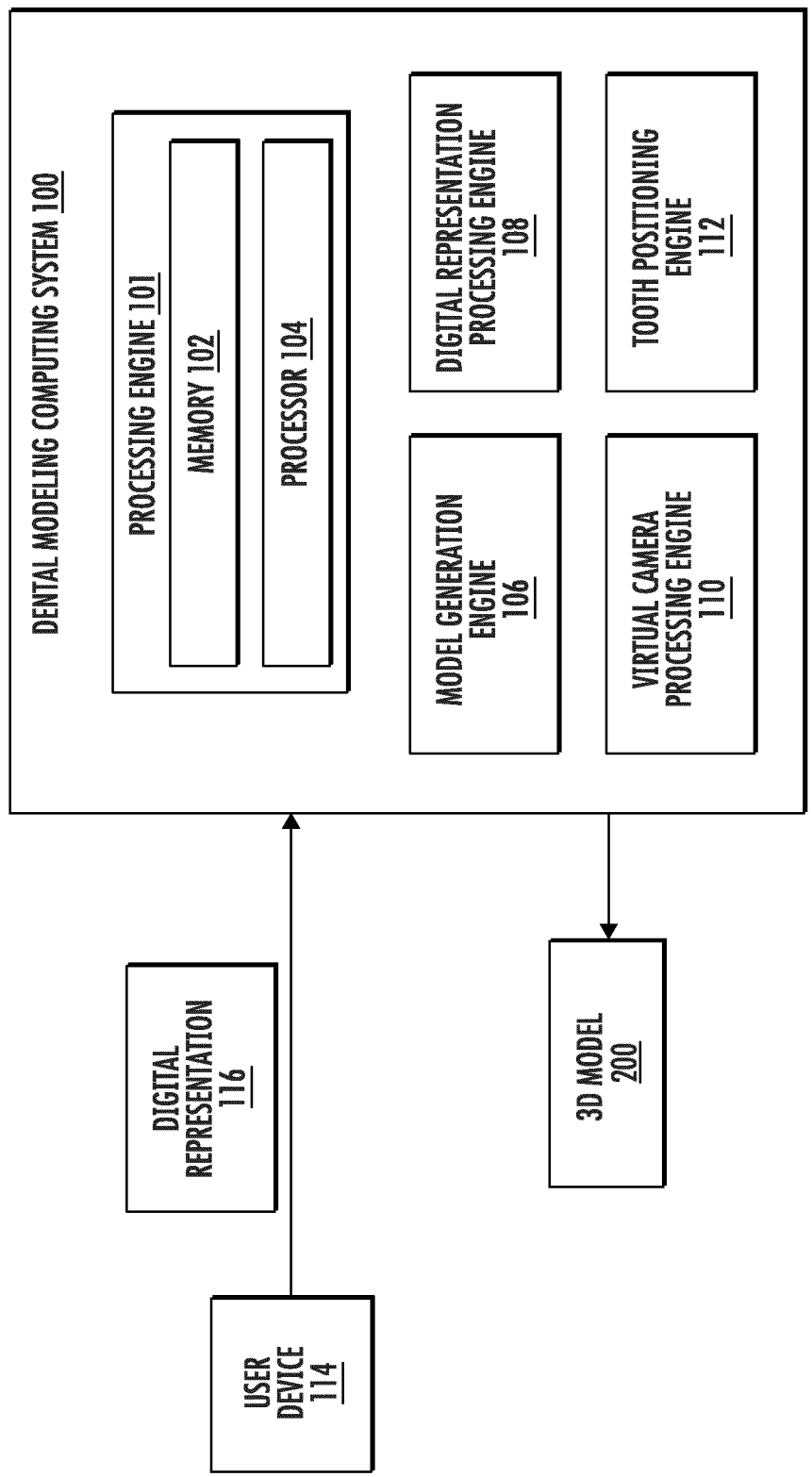
FIG. 1 shows a schematic diagram of a system for dental modeling, according to an illustrative embodiment.

Before turning to the figures, which illustrate certain example embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein are systems and methods for generating a 3D model of a patient's dentition. The systems and methods disclosed herein may be used for purposes of monitoring orthodontic treatment, as well as creation of new treatment plans including, for example, treatment plans for refinements, midcourse corrections, or touch-ups. According to various embodiments, a computing device analyzes one or more digital representations of a dentition (e.g., a 2D image, a plurality of 2D images, a video, a mesh, tabular data, etc.) to determine a position of at least one tooth of the dentition. The digital representation may be captured while the patient is undergoing orthodontic treatment or after the patient has undergone orthodontic treatment. For example, a patient may use an intraoral device (e.g., dental aligner, retainer, braces, etc.) to move at least one tooth from a first position to a second position, or to retain the position of the tooth in the case of a retainer. Based on the position of the at least one tooth from the digital representation, the computing device can move a model tooth of a 3D digital model of a dentition to a position corresponding to the position of the at least one tooth from the digital representation. For example, the computing device may generate a first 3D digital model of a dentition with model teeth in a first position. The first 3D model may correspond with the patient or may be a template model. The computing system may receive a 2D image of the patient's tooth in a position. Based on the 2D image, the computing system can move a corresponding tooth of the 3D digital model from the first position to a second position to represent the position of the patient's tooth from the 2D image. The position of the patient's tooth may be an actual relative 3D position of the patient tooth as reflected in the 2D image.

The technical solutions of the systems and methods disclosed herein improve the technical field of monitoring a patient's dentition and the movement of the patient's teeth due to natural causes or due to orthodontic treatment and devices and the technology associated therewith. For example, in various embodiments, the accuracy, speed, and efficiency of generating a 3D digital model of a patient's dentition is improved. The efficiency is improved by using less data than traditional imaging and monitoring processes and by using data that is captured by the patient instead of captured by a dental professional (e.g., a dental technician, a dentist or orthodontist, or other staff member) at an in-person office visit. For example, the 3D digital model can be based on a template model eliminating the need to obtain data associated with the patient from two separate time periods. Additionally, the data associated with the patient used to generate the 3D model can be captured via a user device associated with the patient (e.g., a camera of a smart phone). This eliminates the need for expensive equipment such as x-rays and intraoral scanners and the need for the patient to visit a professional's office to gather the data necessary to generate the 3D model. The speed of generating models is improved by analyzing all data that is relevant to indicate new positions of teeth. Simultaneous incorporation of all relevant data from multiple sources improves and allows for more informed assessment of teeth positions which leads to a more efficient (therefore, faster) algorithm. For example, a plurality of images may be received from a patient from different imaging angles and combined with prior information about anticipated teeth movements to better govern updating the 3D tooth model. Further, the system does not waste time analyzing images that do not show the corresponding patient tooth, that are too blurry or otherwise obscure the patient tooth, or that only include data that was already provided by a different image (e.g., a duplicate). The accuracy is improved by focusing the analysis and computations on data that is clear and directed toward the immediate task and removing or ignoring data that may differ from or contradict other data. Accuracy is also improved by iteratively solving for a position of a patient tooth shown in a 2D image to account for any distortion, perspective, etc. of the device that captured the image. This ensures the position of the model tooth in the 3D model matches the position of the corresponding tooth from the 2D images.

Furthermore, receiving 2D images from a camera and using only those images that are relevant and useful to the task being performed reduces the computational load on the system and reduces the memory space used to perform the tasks. For example, the computational load is reduced by reducing the amount of data analyzed. Instead of large comprehensive scan files and x-ray files, the system disclosed herein can use 2D images obtained by the patient's own smartphone, including 2D images obtained from videos. Instead of analyzing every image received for determining the location of each tooth, a subset of the images are used based on relevancy, quality, duplicity, etc. The memory space used is reduced by using smaller data files (e.g., 2D image vs. x-ray image, etc.) and deleting or removing data from the system that is not relevant or useful.

Additional benefits of the technical solutions disclosed herein include, but are not limited to, enabling a user to determine when individual teeth are or are not moving (e.g., tooth ankylosis), detecting unwanted tooth movements, and generating an accurate 3D model of a patient's dentition that can be used for various purposes. For example, the 3D model can be used for monitoring a treatment plan, creating a new treatment plan (e.g., refinements, mid-course corrections, touch-ups, etc.), and generating new data that can be used to refine and adapt current protocols for creating new treatment plans. Furthermore, all of this can be done without the need for specialized hardware. For example, a user device (e.g., smartphone) capable of capturing an image can be used to generate the 3D model. The systems and methods disclosed herein require no specialized machines or equipment apart from a smartphone or digital camera. For example, this solution requires no use of x-ray machines, intraoral scanners, impression kits, monitoring scan boxes, etc. The systems and methods also require no specialized training or expertise from a patient or user of the system. The systems and methods also require no knowledge of a treatment plan to generate the 3D model of the patient's dentition. This solution allows treatment progress to be determined remotely and increases patient engagement during the treatment by keeping the user informed (e.g., more frequent status updates regarding tooth movement) and simplifying the process (e.g., no trips to the dentist's office).

Referring to FIG. 1, a dental modeling computing system 100 for generating a digital representation of a patient's dentition is shown, according to an exemplary embodiment. The dental modeling computing system 100 is shown to include a processing engine 101. Processing engine 101 may include a memory 102 and a processor 104. The memory 102 (e.g., memory, memory unit, storage device) may include one or more devices (e.g., RAM, ROM, EPROM, EEPROM, optical disk storage, magnetic disk storage or other magnetic storage devices, flash memory, hard disk storage, or any other medium) for storing data and/or computer code for completing or facilitating the various processes, layers, and circuits described in the present disclosure. The memory 102 may be or include transitory memory or non-transitory memory, and may include database components, object code components, script components, or any other type of information structure for supporting the various activities and information structures described in the present disclosure. According to an illustrative embodiment, the memory 102 is communicably connected with the processor 104 and includes computer code for executing (e.g., by the processor 104) the processes described herein.

The processor 104 may be a general purpose single-chip or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor or any conventional processor, controller, microcontroller, or state machine. The processor 104 may also be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function.

The dental modeling computing system 100 may include various modules or be comprised of a system of processing engines. The processing engine 101 may be configured to implement the instructions and/or commands described herein with respect to the processing engines. The processing engines may be or include any device(s), component(s), circuit(s), or other combination of hardware components designed or implemented to receive inputs for and/or automatically generate outputs based on an initial digital representation of an intraoral device. As shown in FIG. 1, in some embodiments, the dental modeling computing system 100 may include a model generation engine 106, a digital representation processing engine 108, a virtual camera processing engine 110, and a tooth positioning engine 112. While these engines 106-112 are shown in FIG. 1, it is noted that the dental modeling computing system 100 may include any number of processing engines, including additional engines which may be incorporated into, supplement, or replace one or more of the engines shown in FIG. 1.

Figure 2:
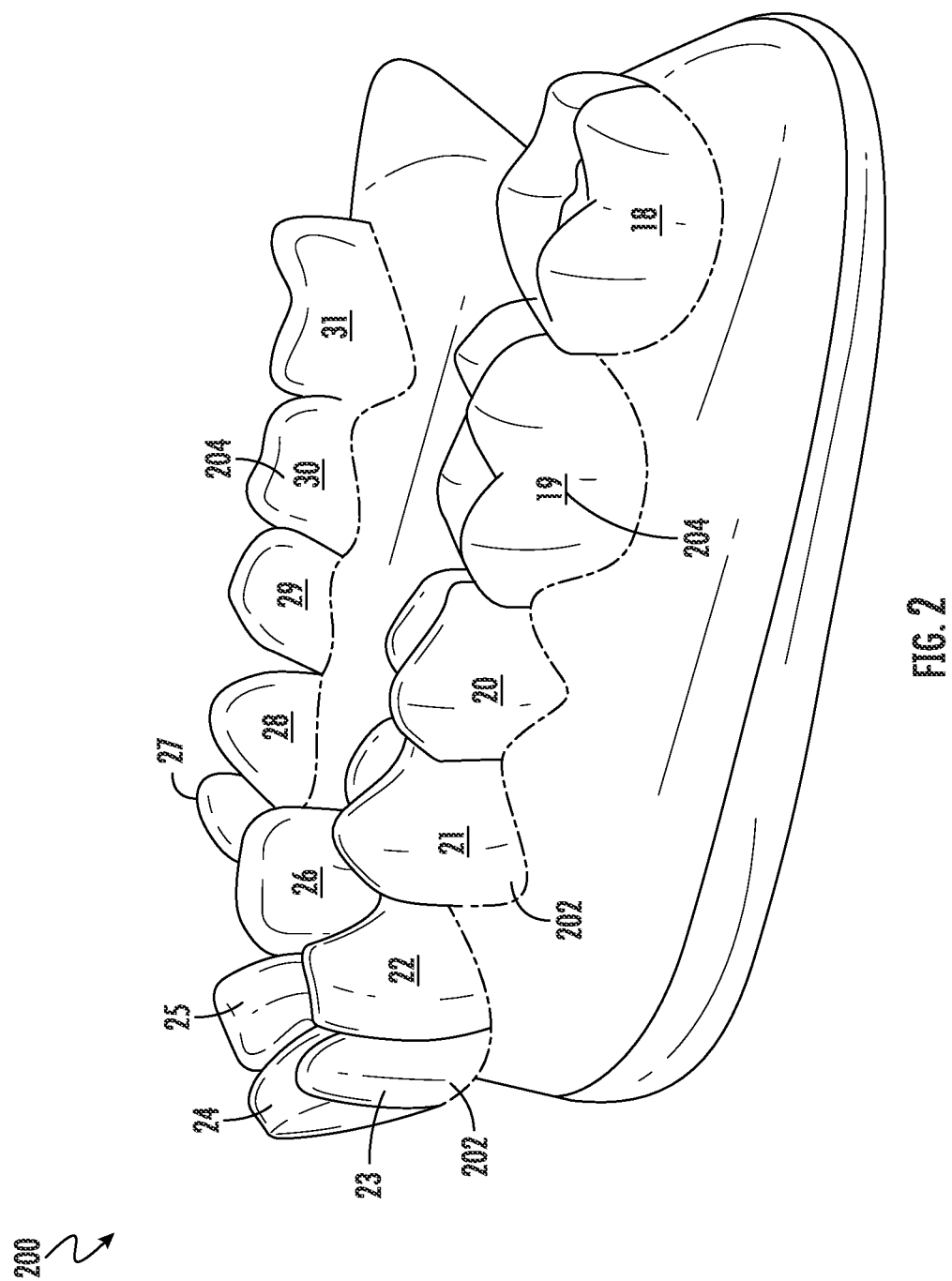
FIG. 2 shows a 3D model of a dentition, according to an illustrative embodiment.

Referring now to FIGS. 1 and 2, dental modeling computing system 100 may be configured to generate a 3D model (e.g., a 3D digital model) of a dentition. For example, model generation engine 106 may be configured to generate a 3D model 200 of a dentition. The 3D model 200 may include a plurality of model teeth 202. The 3D model 200 may include a mesh for a base of the dentition (e.g., the gingiva). The 3D model 200 may include an individual mesh for each individual model tooth 202. The one or more individual model teeth 202 may be based on either a template model (e.g., indicate a generic orientation of a dentition not associated with a patient) or may be based on an actual shape of a patient's dentition (e.g., indicate an actual orientation of a patient's dentition at some point in time). For example, a geometry of a model tooth 202 may be based on previously obtained data from the patient, including but not limited to a 3D scan, an impression, or a picture of the patient's dentition. In another example, the geometry of the model tooth 202 may be based on a template model dentition. For example, memory 102 may include a template dentition library. The template dentition library may include template data of a dentition. For example, the template dentition library may include at least one template model dentition with a template geometry that includes template model teeth 202 with template geometries or data regarding a template dentition (e.g., images, dimensions, geometries, scans, treatment plans, etc. of the template dentition). The template may be obtained from a single case library look-up, or may be based on individual teeth positions using historic treatment plan data. As described herein, the dental modeling computing system 100 may be configured to determine an actual geometry of a patient tooth. As the geometry of a patient tooth is determined, the model generation engine 106 may be configured to modify the shape of the template model tooth 202 to better resemble the actual geometry of the patient tooth. This can be performed for any number of template model teeth.

In some embodiments, the dental modeling computing system 100 may be configured to segment the 3D digital model of the dentition. For example, the model generation engine 106 may be configured to segment 3D digital model 200 of the dentition. For example, 3D digital model 200 may include a plurality of model teeth 202. Model generation engine 106 may be configured to identify individual model teeth 202 of the 3D digital model 200. The model generation engine 106 may assign a label 204 to each model tooth 202. For example, the label 204 may include tooth numbers according to, for example, FDI World Dental Federation notation, the universal numbering system, Palmer notation, or any other labeling/naming convention.

Referring now to FIGS. 1 and 3, the dental modeling computing system 100 may be configured to receive at least one digital representation 116 of a dentition. For example, digital representation processing engine 108 of the dental modeling computing system 100 may be configured to receive at least one digital representation 116 of a dentition. The dentition may be associated with a patient. The digital representation 116 may include data corresponding to a plurality of patient teeth. For example, the digital representation 116 may be a 2D image, a video, a mesh, tabular data, or population-level information about most probable tooth movements, among others. The 2D image and video may be captured by any device capable of capturing images and videos (e.g., a smart phone). The tabular data may include, for example, a patient's subjective assessment of dental aligner fit. In some embodiments, the digital representation processing engine 108 may receive a plurality of digital representations 116. The plurality of digital representations 116 may include at least one of a plurality of individually taken images or a video. For example, the digital representation processing engine 108 may receive a plurality of 2D images. In some embodiments, the plurality of digital representations 116 may include images of the same dentition from different perspectives. In some embodiments, the plurality of digital representations 116 may include images of the same dentition with different expressions. For example, a digital representation processing engine 108 may receive a first 2D image including a perspective view 302 of the dentition. The digital representation processing engine 108 may receive a second 2D image including a full front view 304 of the dentition. The full front view 304, for example, may include both top and bottom teeth of the dentition. For example, a patient may use a lip retractor (e.g., a dental appliance, patient's fingers, household items, etc.) such that all teeth, and all visible portions of the teeth that are visible from a front view are shown in the second 2D image. The dental appliance can be configured to hold open the user's upper and lower lips simultaneously to permit visualization of the user's teeth and further configured to continue holding open the user's upper and lower lips in a hands-free manner after being positioned at least partially within the user's mouth. The dental appliance can include a single handle having two ends and a pair of flanges at each end of the handle, each pair of flanges can be U-shaped, thereby forming a cavity between the flanges, and each cavity can be configured to receive a portion of the user's upper and lower lips. The handle can be arch-shaped such that when the dental appliance is positioned at least partially within the user's mouth to hold open the user's upper and lower lips the handle does not obstruct the user's open mouth such that the handle does not obstruct any of the user's teeth when one or more photos are taken of the user's mouth from a front view. A length of the handle, a size of the flanges, and a size of each cavity between the flanges can be adjustable or non-adjustable. The dental appliance can be formed as a single unitary component or made up of separate and discrete components.

The digital representation processing engine 108 may receive a third 2D image including a partial front view 306 of the dentition. The partial front view 306, for example, may include only the top or only the bottom teeth of the dentition. The digital representation processing engine 108 may be configured to receive any number and any combination of digital representations 116 of the dentition. In some embodiments, the digital representation processing engine 108 may receive a video of a plurality of patient teeth. The digital representation processing engine 108 may be configured to transform the video into a plurality of 2D images.

The digital representation processing engine 108 may be configured to receive the at least one digital representation 116 from an external computing system, such as user device 114. Examples of the user device 114 may include, but are not limited to, a mobile phone a tablet computer, a laptop computer, a smart watch, or any other internet-connected device. The user device 114 can be a personal user device 114 of a patient. For example, the user device 114 can be the patient's own mobile phone. The user device 114 may be configured to capture the digital representation 116. For example, the user device 114 may include a camera configured to capture a 2D image. The user device 114 may be configured to transmit the digital representation 116 and the digital representation processing engine 108 may be configured to receive the digital representation 116 from the user device 114. The user device 114 may capture digital representations 116 by using similar processes to those described in U.S. patent application Ser. No. 17/581,811, titled "Machine Learning Architecture for Imaging Protocol Detector," filed Jan. 21, 2022, the contents of which are incorporated herein by reference in its entirety.

The user device 114 may be configured to send communications to, and receive communications from, a cloud server. The user device 114 may communicate to, and receive communications from the cloud server by using similar processes to those described in U.S. patent application Ser. No. 16/711,173, titled "Scanning Device," filed Dec. 11, 2019, the contents of which are incorporated herein by reference in its entirety. For example, the user device 114 can communicate information regarding images captured or received from other computing devices to the cloud server such that the cloud server can perform further operations. The user device 114 can communicate with the cloud server in a variety of ways including, but not limited to, Bluetooth, a WiFi network, a wired local area network (LAN), Zigbee, or any other suitable way for devices to exchange information. In some embodiments, the user device 114 includes a radiofrequency transceiver to communicate with one or more radio towers to transmit and/or receive information using radio waves. In some embodiments, the radiofrequency transceiver includes a single band transceiver. In some embodiments, the radiofrequency transceiver includes a dual band transceiver.

The cloud server may be communicably coupled to the user device 114. In addition to being communicably coupled to the user device 114, the cloud server can be communicably coupled to a plurality of user devices 114. The cloud server may be configured to receive digital representations 116 from the user device 114 and perform additional operations on the data in order to prepare the digital representations to send to the dental modeling computing system 100. The additional operations the cloud server can perform include, but are not limited to, high-resolution reconstruction of digital representations 116 and converting the digital representation 116 to one or more 3D images. The cloud server can communicate the results of the additional operations to the dental modeling computing system 100.

In addition, the cloud server may be configured to analyze the data received from the plurality of user devices 114 to which the cloud server is communicably coupled, and provide the output of the analysis to the dental modeling computing system 100 via the user device 114. For example, the cloud server may determine, based on the analysis of a plurality of digital representations, that patients must hold a camera within a certain angular tolerance. The cloud server can provide that information to user device 114 such that patient can capture digital representations 116 from the proper orientation. The dental modeling computing system 100 may also be communicably coupled to the cloud server and may be configured to receive the digital representations 116 from the cloud server and generate one or more 3D models based on the digital representations 116.

A tower network may include a plurality of towers. The towers can be referred to as cellular towers, radio towers, base stations, base transceiver stations, etc., and include equipment for cellular communication. For example, the towers may include various antennae, transmitters, receivers, transceivers, digital signal processors, control electronics, global positioning receivers, and electrical power sources. The towers may be configured such that each of the towers can send and receive signals within a specified area (e.g., a cell). Typically, the area in which each of the towers can send and receive signals is shaped approximately like a hexagon. For example, a first tower can send and receive signals (e.g., data) within a first area, a second tower can send and receive signals within a second area, and a third tower can send and receive signals within a third area. To send a signal from an originating location to a destination location, each tower can send a signal to a tower within an adjacent area. For example, the first tower can send a signal to the second tower when the first area is adjacent to the second area.

The user device 114 may transmit signals (e.g., radio signals containing data related to a digital representation 116) to communicate with the cloud server. For example, when the user device 114 is within the first area, the signal reaches the first tower. From the first tower, the signal may be sent to the second tower because the first area is adjacent to the second area, and from the second tower the signal may be sent to the third tower because the second area is adjacent to the third area.

In some embodiments, the signals sent by the user device 114 include multiple digital signals, multiple analog signals, or a combination of multiple digital and analog signals. In such embodiments, the multiple signals are combined into one signal using multiplexing protocols to reduce the resources required to send the signal. In an example embodiment, frequency division multiplexing (FDM) can be used to combine the signals. In FDM, each user is assigned a different frequency from the complete frequency spectrum such that all frequencies can travel simultaneously. In another example embodiment, time division multiplexing (TDM) can be used to combine the signals. In TDM, a single radio frequency is divided into multiple slots and each slot is assigned to a different user such that multiple users can be supported simultaneously. In yet another example embodiment, code division multiplexing (CDMA) can be used to combine the signals. In CDMA, several users share the same frequency spectrum simultaneously and are differentiated via unique codes assigned to each user. The receiver is supplied with the unique keys such that the user can be identified by the receiver.

In some embodiments, the signal is sent via a packet switching process. In a packet switching process, the signal (e.g., the data being sent) is divided into smaller parts called packets. The packets are then sent individually from the source (e.g., the user device 114) to the destination (e.g., the cloud server). In some embodiments, each packet can follow a different path to the destination, and the packets can arrive out of order at the destination, where the packets are assembled in order (e.g., a datagram approach). In some embodiments, each packet follows the same path to the destination, and the packets arrive in the correct order (e.g., a virtual circuit approach).

Accordingly, any data acquired by the user device 114 can be communicated to the cloud server or the dental modeling computing system 100 by way of or not by way of a cloud server using the tower network. In some embodiments, the processes performed by dental modeling computing system 100 can be performed by the cloud server. In some embodiments, any data acquired by the user device 114 can be communicated using one or more towers of the tower network. For example, digital representation 116 of the user's teeth captured by the user device 114 can be communicated to the cloud server or the dental modeling computing system 100 by way of one or more towers of the tower network. Additionally, digital representations of the user's teeth captured by the user device 114 can be communicated directly to other locations (e.g., the office of a dental professional, etc.) by way of one or more of the towers for diagnostic purposes, treatment purposes, or any other purpose. In some cases, communicating digital representation data over the tower network is advantageous over other methods of communication. For example, the digital representation data can be more efficiently communicated when broken up into smaller sized packets or smaller file sizes and separately communicated over the tower network rather than being communicated in a large file size or larger packets when using other methods of communication.

In some embodiments, the digital representation processing engine 108 may be configured to filter the digital representations 116. For example, the digital representation processing engine 108 may receive a plurality of digital representations 116. The digital representation processing engine 108 may be configured to designate a subset of the digital representations 116 as at least one of useful or not useful. For example, a digital representation 116 designated as useful may be focused (e.g., clear, not blurry) such that the digital representation processing engine 108 may clearly identify individual teeth. A digital representation 116 designated as not useful may be out of focus or too blurry to distinguish between teeth. In some embodiments, a digital representation 116 designated as not useful may include teeth that are not going to be analyzed by the digital representation processing engine 108. For example, when the digital representation processing engine 108 is to analyze a bottom jaw of a patient, digital representations 116 including only teeth of the top jaw can be designated as not useful. In some embodiments, a digital representation 116 designated as not useful may be a duplicate of another digital representation 116. A duplicate digital representation 116 may include substantially the same information as another digital representation 116. For example, a first digital representation 116 may include the same perspective, expression, camera parameter (described in more detail below), etc., or any combination thereof as a second digital representation 116. A digital representation 116 may be designated as a duplicate when the digital representation processing engine 108 determines that information from a first digital representation 116 can be obtained from a second digital representation 116. The digital representation processing engine 108 may be configured to apply a threshold to determine whether a digital representation 116 is a duplicate. For example, if a predetermined percentage (e.g., 90%) of the information from a first digital representation 116 can be obtained from a second digital representation 116, the digital representation processing engine 108 may determine the first digital representation 116 is a duplicate.

The digital representation processing engine 108 may be configured to ignore the subset of the plurality of digital representations 116 designated as not useful. In one embodiment, the digital representation processing engine 108 may be configured to store the subset of the plurality of digital representations 116 that are designated as not useful in the memory 102 of the dental modeling computing system 100. The dental modeling computing system 100 may be configured to perform further analysis, computations, processing, etc. on the subset designated as useful while not performing the analysis, computations, processing, etc., on the subset designated as not useful. For example, the dental modeling computing system 100 may be configured to determine a second position of a model tooth based on the subset of the plurality of digital representations associated with the corresponding patient tooth. This technological solution reduces the computational bandwidth needed to perform the methods disclosed herein by reducing the quantity of computations the dental modeling computing system 100 performs by reducing the number of digital representations 116 the dental modeling computing system 100 analyzes, processes, computes, etc.

In other embodiments, the digital representation processing engine 108 may be configured to delete or remove the subset of the plurality of digital representations 116 that are designated as not useful. For example, the digital representation processing engine 108 can remove the subset of the plurality of digital representations 116 that are designated as not useful from the dental modeling computing system 100. Along with reducing the computational bandwidth needed to perform the methods disclose herein, this technological solution reduces the amount of storage needed to store and analyze the digital representations 116 by removing the not useful digital representations 116 from the system.

Figure 4:
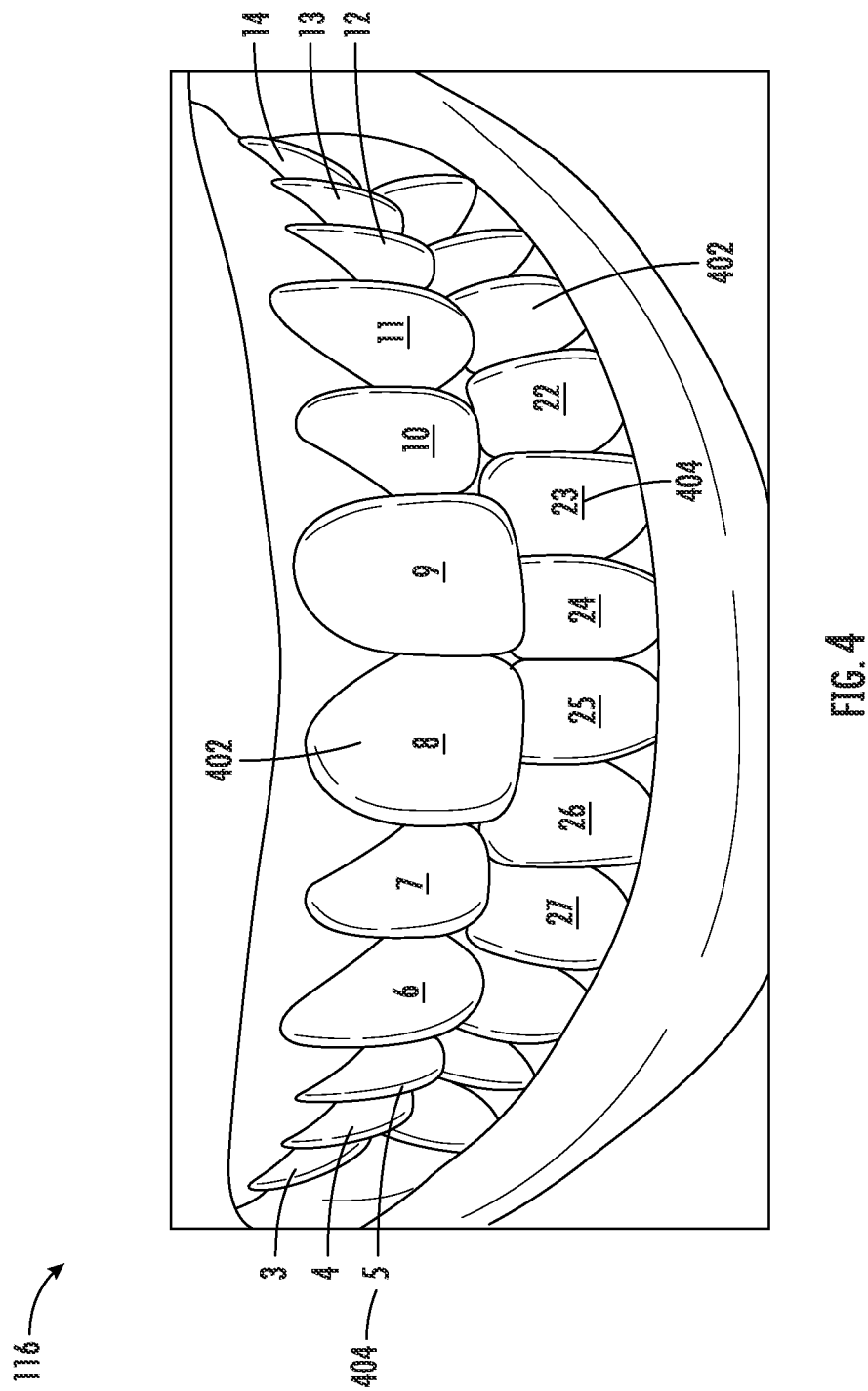
FIG. 4 shows a digital representation, according to an illustrative embodiment.

Referring now to FIGS. 1 and 4, the digital representation processing engine 108 may be configured to segment teeth from the digital representation 116. Similar to the segmentation described with reference to FIG. 2 regarding the 3D digital model 200, the digital representation processing engine 108 may be configured to segment the digital representation 116. For example, the digital representation 116 can be a 2D image of a patient's dentition. The 2D image may include a plurality of patient teeth 402. The digital representation processing engine 108 may be configured to identify the individual patient teeth 402 of the 2D image. The digital representation processing engine 108 may assign a label 404 to each individual patient tooth 402. The digital representation processing engine 108 may apply a labeling convention to the patient teeth based on the labeling convention applied by the model generation engine 106 to the model teeth 202 (e.g., the model teeth 202 are labeled according to the same labeling convention as the patient teeth 402).

In some embodiments, the digital representation processing engine 108 may be configured to organize or classify a plurality of digital representations 116 based on content of each of the plurality of digital representations 116. For example, the digital representation processing engine 108 may associate a subset of the plurality of digital representations 116 with a corresponding patient tooth 402. For example, the digital representation processing engine 108 may identify the subset of the plurality of digital representations 116. The subset of the plurality of digital representations 116 may include the digital representations 116 that show a first patient tooth 402. In some embodiments, the digital representation processing engine 108 may associate a digital representation 116 including the first patient tooth 402 with the first patient tooth 402. In some embodiments, the subset of the plurality of digital representations 116 may include the digital representations 116 that show a predetermined portion of the first patient tooth 402. The digital representation processing engine 108 may associate the digital representation 116 with the first patient tooth 402 if at least the predetermined portion of the first patient tooth 402 is shown in the digital representation 116. The predetermined portion may be configured to identify digital representations 116 wherein the patient tooth 402 is unobstructed enough to obtain positioning data of the patient tooth 402. For example, the digital representation processing engine 108 may associate the digital representation 116 with the first patient tooth 402 if fifty percent of a face of the first patient tooth 402 is visible. However, it will be appreciated that the percentage can be any predefined number (e.g., ten percent, twenty percent, fifty percent, seventy percent, ninety percent, etc.). In another example, the digital representation processing engine 108 may associate the digital representation 116 with the first patient tooth 402 if 50 mm$^2$ of the first patient tooth 402 is visible. However, it will be appreciated that the surface area can be any predefined number (e.g., 5 mm$^2$, 10 mm$^2$, 20 mm$^2$, 30 mm$^2$, 50$^2$, 80 mm$^2$, etc.). For example, referring to FIG. 4, the digital representation processing engine 108 may associate the digital representation 116 with Tooth 8 since a whole front surface of Tooth 8 is visible. The digital representation processing engine 108 may not associate the digital representation 116 with Tooth 14 because only a small portion of Tooth 14 is visible. However, referring to FIG. 3, the digital representation processing engine 108 may associate perspective view 302 with Tooth 14 since a majority of the surface of Tooth 14 is visible. Associating a subset of the plurality of digital representations 116 with a patient tooth 402 can reduce the quantity of calculations the digital representation processing engine 108 performs when determining a position of the patient tooth 402 by reducing the number of digital representations 116 to be analyzed and removing digital representations 116 that may provide contradictory or unhelpful positioning data.

In some embodiments, the dental modeling computing system 100 may be configured to associate a model tooth 202 with a patient tooth 402. For example, the digital representation processing engine 108 of the dental modeling computing system 100 may be configured to associate a model tooth 202 with a patient tooth 402. Based on the segmentation of the 3D digital model 200 and the digital representation 116, the digital representation processing engine 108 may associate a model tooth 202 with a patient tooth 402 that has a corresponding label 204, 404. For example, the digital representation processing engine 108 may associate Model Tooth 22 with Patient Tooth 22. In some embodiments, the digital representation processing engine 108 can detect when the digital representation 116 is segmented incorrectly. For example, the digital representation 116 may be blurry such that the digital representation processing engine 108 cannot identify a space between two patient teeth 402, resulting in the digital representation processing engine 108 identifying the two patient teeth 402 as a single patient tooth 402. The digital representation processing engine 108 may detect an incorrect segmentation and reject the label 204 if the label 204 falls outside of population norms (e.g., corresponds with a tooth that is too large or too small for the location), if the classifier likelihood for detection is too low, or because the label does not overlap well with a corresponding object in a projected 3D mesh. For example, to correctly label the digital representation 116, the digital representation processing engine 108 may be configured to overlay the 3D digital model 200 (e.g., a 3D mesh) with the digital representation 116. The digital representation processing engine 108 may be configured to project a label from the 3D digital model 200 on to the digital representation 116. The digital representation processing engine 108 may be configured to reject a label in the digital representation 116 if the correspondence of the digital representation 116 with the projected 3D model 200 is sufficiently poor (e.g., the objects do not overlap or overlap very little). If a label is wrong, but overlaps sufficiently with a different model tooth 202 in the projected 3D mesh, the digital representation processing engine 108 may determine that the label is correct for the different object. The digital representation processing engine 108 may label the digital representation 116 based on the label(s) of the 3D digital model 200.

In some embodiments, the dental modeling computing system 100 may be configured to designate a feature of a digital representation 116 as an obstruction. For example, the digital representation processing engine 108 of the dental modeling computing system 100 may be configured to designate a feature of the digital representation 116 as an obstruction. An obstruction may be a feature of the digital representation 116 that blocks a view of a portion of the patient dentition. The feature may not directly affect or participate in the positioning of patient teeth. For example, an obstruction can include lips, tongue, a dental appliance, fingers, or other elements that may be captured in the digital representation 116 but does not engage in the positioning of the teeth. The dental appliance can be configured to hold open the user's upper and lower lips simultaneously to permit visualization of the user's teeth and further configured to continue holding open the user's upper and lower lips in a hands-free manner after being positioned at least partially within the user's mouth so that the patient or a third party is able to capture digital representations of the patient's teeth. As explained in more detail below, the features designated as obstructions may affect the movement, and specifically penalties applied to the movement, of the model teeth 202 of the 3D digital model 200.

Figure 5:
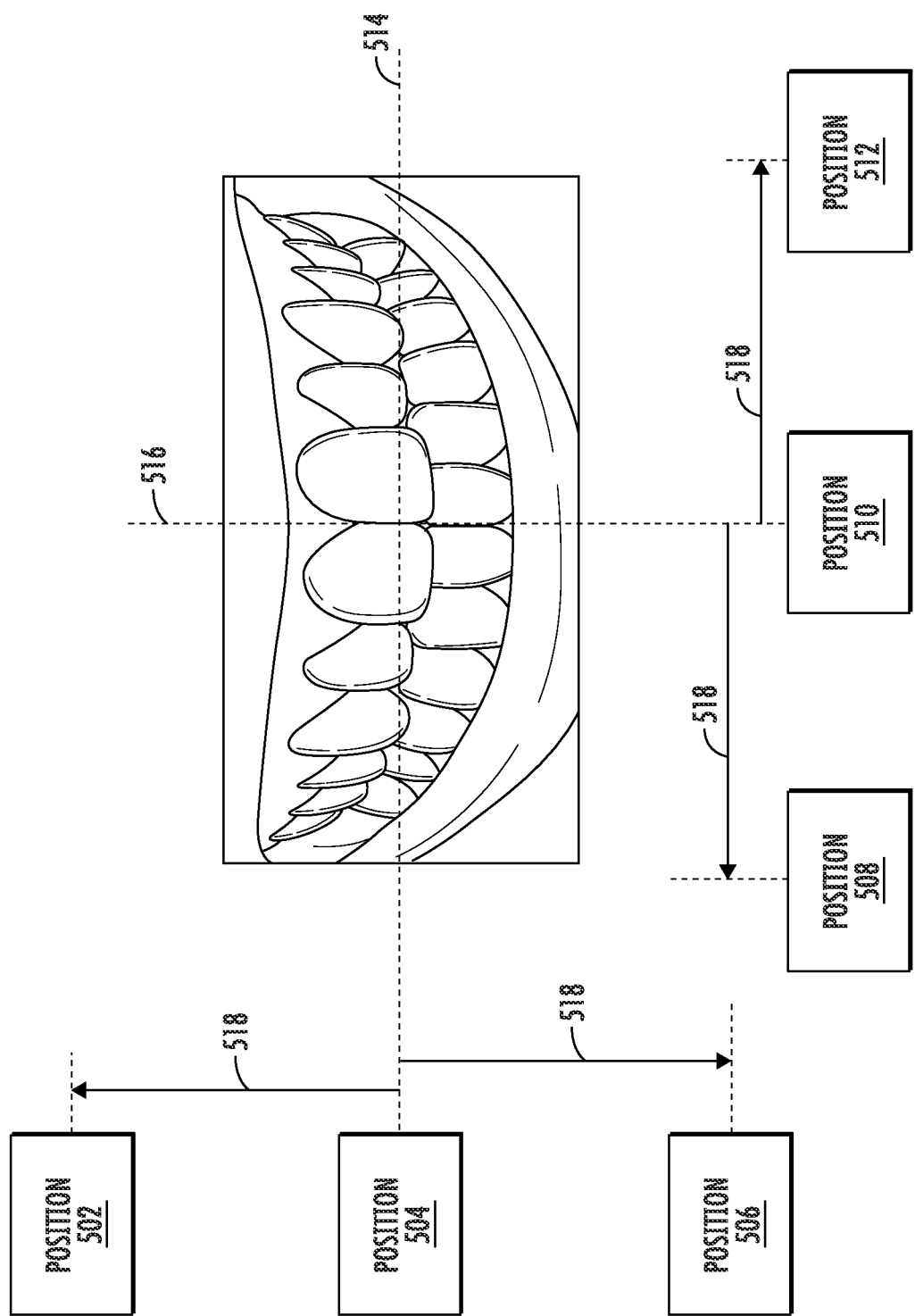
FIG. 5 shows an extrinsic virtual camera parameter, according to various illustrative embodiments.

Referring now to FIGS. 1, and 5-7, the dental modeling computing system 100 may be configured determine at least one virtual camera parameter associated with a virtual camera. The virtual camera parameter may include at least one value that is representative of a setting of a virtual camera. The virtual camera parameter may correspond with a parameter of a device (e.g., a camera of user device 114) used to capture a digital representation 116. For example, a virtual camera parameter may include an extrinsic parameter and/or an intrinsic parameter. Extrinsic parameters may correspond with a position and/or orientation of the virtual camera. For example, an extrinsic parameter may define at least one of a translational matrix or a rotational matrix of a camera of a user device 114. For example, for the translational matrix, the extrinsic parameter may define a location of the camera when the digital representation was captured. For example, the user device 114 may be aligned with or have an offset from a centerline of the patient's dentition. FIG. 5 shows a plurality of examples of virtual camera parameters. The virtual camera parameters may be associated with locations at which a camera of the user device 114 can be when capturing a digital representation 116. For example, when at position 502, the camera may have an offset 518 (e.g., be vertically above) from a horizontal centerline 514 of the patient's dentition. At position 504, the user device 114 may be in line with (have no offset 518) the horizontal centerline 514. At position 506, the camera may have an offset 518 (e.g., be vertically below) the horizontal centerline 514. At position 508, the camera may have an offset 518 (e.g., to the left) from a vertical centerline 516 of the patient's dentition. At position 510, the camera may be aligned with (have no offset 518) the vertical centerline 516. At position 512, the camera may have an offset 518 (e.g., to the right) from the vertical centerline 516.

Figure 6:
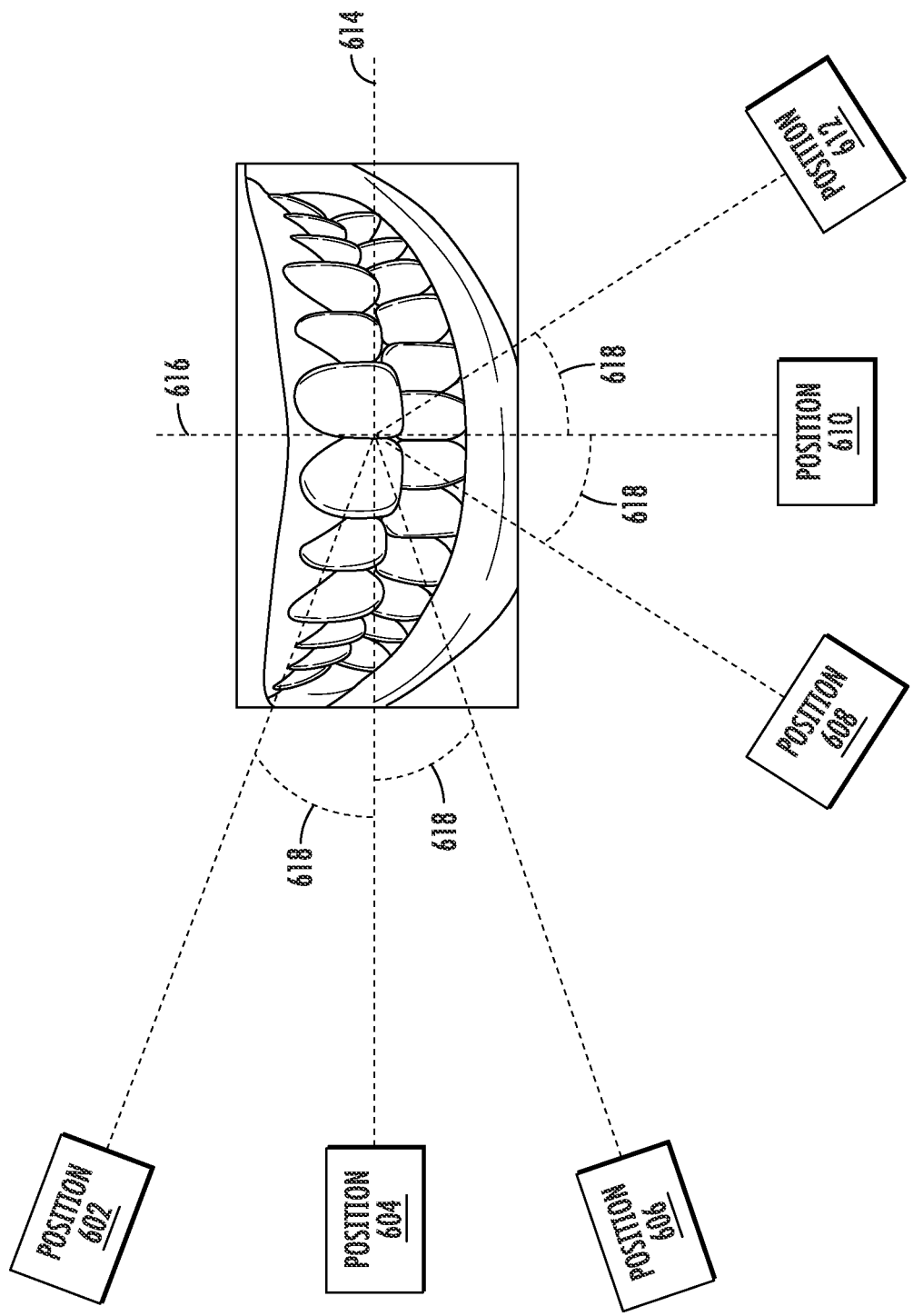
FIG. 6 shows an extrinsic virtual camera parameter, according to various illustrative embodiments.

In some embodiments, for the rotational matrix, the extrinsic parameter may define an orientation (e.g., an angle) of a camera of the user device 114. For example, the camera may be parallel with or set at an angle from a center plane of the patient's dentition. FIG. 6 shows a plurality of examples of virtual camera parameters. The virtual camera parameters may be associated with orientations at which the camera may be when capturing a digital representation 116. For example, at position 602, the camera may be rotated downward at an angle 618 from horizontal plane 614 defined by the patient's dentition. At position 604, the camera may be angled parallel with the horizontal plane 614. At position 606, the camera may be rotated upward at an angle 618 from the horizontal plane 614. At position 608, the camera may be rotated to the right at an angle 618 from the vertical plane 616. At position 610, the camera may be angled parallel with the horizontal plane 614. At position 612, the camera may be rotated to the left at an angle 618 from the vertical plane 616.

Figure 7:
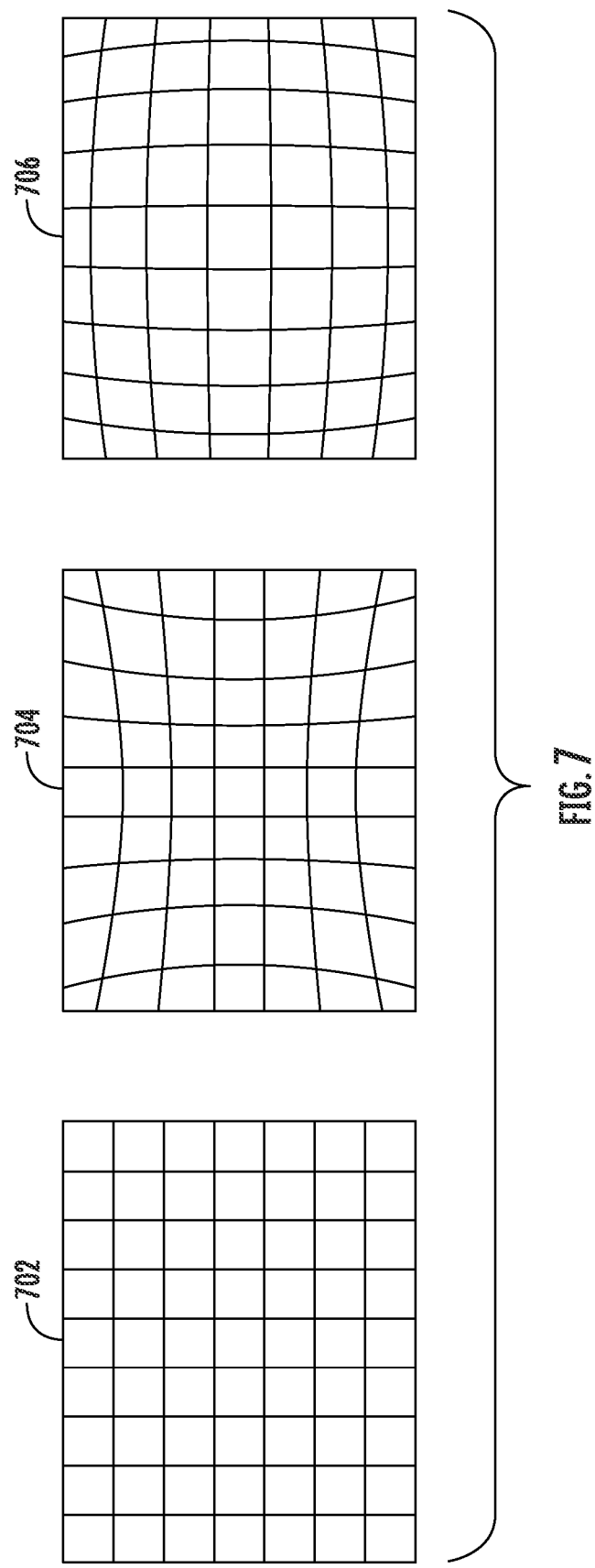
FIG. 7 shows an intrinsic virtual camera parameter, according to various illustrative embodiments.

Intrinsic parameters may correspond with how the virtual camera manipulates a digital representation 116. For example, an intrinsic parameter may define at least one of a perspective or a distortion of a camera (e.g., a camera of a user device 114). For example, a camera may be configured to distort a digital representation 116 wherein the data captured in the digital representation 116 deviates from reality (e.g., straight lines in reality become curved lines in the digital representation 116). FIG. 7 shows an undistorted image 702, a pincushion distortion image 704, and a barrel distortion image 706. The camera may apply a pincushion distortion to a digital representation 116 such that lines that do not run through a center if the digital representation is bowed inward toward the center of the digital representation 116. The camera may apply a barrel distortion to the digital representation 116 such that image magnification decreases with distance away from an optical axis. The camera may apply any variation and combination of distortions to the digital representation 116. The application of a distortion to a digital representation 116 may render a position, size, or orientation, etc. of a patient tooth 402 in the digital representation 116 to be different than in the patient's actual dentition.

The virtual camera processing engine 110 may be configured to determine a virtual camera parameter associated with a virtual camera. The virtual camera parameter may correspond with a parameter of a device (e.g., a camera) used to capture a digital representation 116. In some embodiments, the virtual camera processing engine 110 may receive the virtual camera parameter. For example, the virtual camera processing engine 110 may receive an input indicating a camera setting corresponding to how the camera deals with, applies, or responds to distortions. For example, a camera may include a setting indicating a picture height distortion. The picture height distortion may be a ratio of bending of a straight line over a height of a picture. The virtual camera processing engine 110 may receive a value of the picture height distortion from the input. The input can include any values associated with distortion or perspective settings of the camera. In another example, the position of the camera when capturing the digital representation 116 may also be received as an input. For example, the input may indicate that the camera was directly in front of the patient's dentition when capturing the digital representation 116 or the input may indicate the translational and/or rotational offset the camera had when capturing the digital representation.

In some embodiments, the virtual camera processing engine 110 can calculate the virtual camera parameter. For example, the virtual camera processing engine 110 may be configured to calculate the intrinsic parameters. For example, the dental modeling computing system 100 may receive a plurality of digital representations 116. The dental modeling computing system 100 may be configured to determine a position of a patient tooth 402 by analyzing the plurality of digital representations 116. However, the digital representation processing engine 108 may determine a first position of the patient tooth 402 in a first digital representation 116 is different than a second position of the patient tooth 402 in a second digital representation 116. The virtual camera processing engine 110 may be configured to compare the difference between the first position and the second position and determine a distortion value from the comparison. Upon determination of the distortion value, the distortion value can be applied to other digital representations 116 in order for the dental modeling computing system 100 to determine a correct position of the patient tooth 402. The virtual camera processing engine 110 may also be configured to calculate the extrinsic parameters. Based on a digital representation 116, the virtual camera processing engine 110 may be configured to identify the location and orientation of the camera with respect to the patient's dentition when the digital representation 116 was captured.

In some embodiments, the virtual camera parameter may be determined in one step and applied to the virtual camera such that correct positions of the patient teeth 402 can be determined. For example, the virtual camera processing engine 110 may receive the distortion settings of the camera and apply those settings to the virtual camera to optimize the geometry of the patient teeth 402 from the digital representations 116 to more accurately reflect a true geometry of the teeth. In other embodiments, the determination of the virtual camera parameter may be an iterative process. For example, the iterative process may include a plurality of virtual camera parameter adjustments. For example, the virtual camera processing engine 110 may estimate a virtual camera parameter based on a first digital representation 116. The virtual camera processing engine 110 may then adjust the virtual camera parameter based on a second digital representation 116. The virtual camera processing engine 110 may adjust the virtual camera parameter any number of times. For example, the virtual camera processing engine 110 may adjust the virtual camera parameter for every digital representation 116 that is analyzed. In some embodiments, the virtual camera processing engine 110 may adjust the virtual camera parameter until there are minimal adjustments to be made. For example, the size of the adjustments for each digital representation 116 has become less than a threshold value such that the virtual camera processing engine 110 can determine the virtual camera parameter is accurate (e.g. within a predetermined standard deviation).

Determining the virtual camera parameters may account for distortion of the digital representation 116. The distortion may be caused by the device that captured the digital representation 116. For example, the digital representation 116 may include an image of a patient's dentition that deviates from how the patient's dentition actually looks. Without correction, the deviation may cause the dental modeling computing system 100 to determine the patient tooth is in a different location and/or has a different orientation than it actually does. For example, a digital representation 116 captured with a camera applying a pincushion distortion may include a patient tooth 402 near the center of the digital representation 116 with little or no deformation and a patient tooth 402 near an outer edge of the digital representation 116 with a larger amount of deformation due to the distortion applied by the camera. The virtual camera processing engine 110 can apply the virtual camera parameters to the patient tooth 402 with the large amount of deformation to optimize the geometry of the patient tooth 402. For example, applying the virtual camera parameters can determine how the patient tooth 402 looks in reality versus how it looks in the digital representation 116. The determination of the virtual camera parameters enables the dental modeling computing system 100 to receive digital representations 116 with various distortions, from various perspectives, etc. and optimize the geometry of the teeth in the digital representations 116 to determine an accurate geometry and an accurate position of the patient's teeth. As the virtual camera processing engine 110 adjusts the geometry of a patient tooth 402, the model generation engine 106 may be configured to adjust the geometry of a corresponding model tooth 204 of the 3D model 200 to better reflect the actual geometry of the patient tooth 402. For example, a geometry of a model tooth 202 from a template dentition can be updated to match a geometry of a corresponding patient tooth 402. Therefore, the dental modeling computing system 100 may generate a 3D digital model 200 that resembles a patient's dentition without any previous knowledge thereof. Determination of the virtual camera parameters improves the accuracy of the dental modeling computing system 100 because a distorted digital representation 116 without correction or consideration of the intrinsic and extrinsic parameters of the camera that captured the digital representation 116 would result in incorrect determination of positions and/or geometries of patient teeth 402 and therefore incorrect positioning of model teeth 202.

Figure 8:
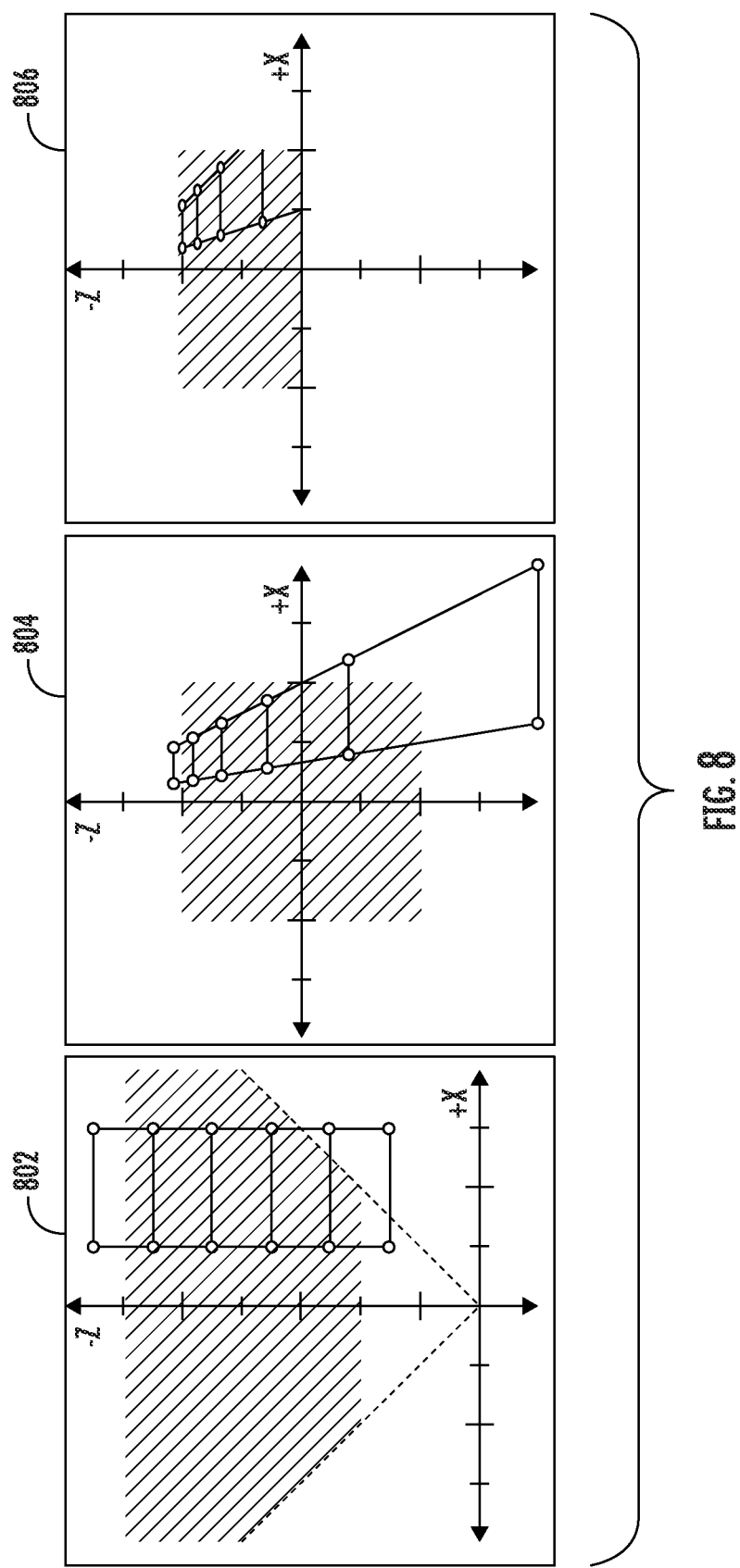
FIG. 8 shows dentition data disposed in a normalized device coordinate space, according to an illustrative embodiment.

Referring now to FIGS. 1 and 8, the dental modeling computing system 100 may be configured to compare a first position of a model tooth 202 from a 3D model 200 with a position of a corresponding patient tooth 402 from a digital representation 116. For example, the tooth positioning engine 112 may be configured to compare the first position of the model tooth 202 with the position of the corresponding patient tooth 402. In some embodiments, tooth positioning engine 112 may use a normalized device coordinate (NDC) space to compare the position of the model tooth 202 with the position of the corresponding patient tooth 402. FIG. 8 depicts a transformation of an image between a camera space 802 and a NDC space 806, according to an exemplary embodiment. Camera space 802 may illustrate a space as seen from a camera's (or a person's) point of view. For example, the camera space 802 can resemble a 2D image. The coordinate system of the camera space 802 may be defined by a position or axis of the camera. Camera space 802 may be transformed into a 3D camera space 804. The 3D camera space 804 may illustrate the same space as the camera space 802, but in a 3D coordinate system. The 3D camera space 804 may be transformed into the NDC space 806. The NDC space 806 can crop the space from the camera space 802 and only include the portion disposed within the defined NDC space 806. In some embodiments, the NDC space 806 may be defined with a coordinate system ranging from (−1, −1, −1) to (1, 1, 1). In other embodiments, the transformation may instead move from a 3D space to a 2D space and the 2D space can be normalized. For example, the NDC space may be defined with a coordinate system of (−1, −1) to (1, 1).

In some embodiments, a 3D model may include a 3D mesh. The tooth positioning engine 112 may render down the 3D mesh into the NDC space 806. For example, the 3D mesh may be flattened into a point cloud and normalized in the NDC space. The tooth positioning engine 112 may also interpret the segmentation of the 2D digital representation 116 performed by the digital representation processing engine 108 as a polygon. A boundary of the polygon may also be disposed and normalized in the NDC space. The tooth positioning engine 112 may project identified keypoints on the 2D digital representation 116 to normalized NDC space. When the 3D mesh (illustrating the first position of the model tooth 202) and the 2D polygon or keypoints (illustrating the position of the corresponding patient tooth 402) are in the NDC space, the tooth positioning engine 112 may calculate an error metric between the 3D mesh and the 2D polygon or keypoints. The error metric can define a difference between the first position of the model tooth 202 and the position of the corresponding patient tooth 402. For example, the error metric can determine how much the model tooth 202 will have to move and in which directions the model tooth 202 will have to move in order to match the position of the corresponding patient tooth 402.

The 3D model 200 may be updated using an optimizer. The optimizer may use one or more error metrics and constraints. For example, a stochastic gradient descent may be applied to update the 3D model based on the error metric. Optimizer constraints may include penalties to dissuade improbable tooth movements. Optimizer constraint penalties may be informed from customer-specific information or population-specific information. For example, customer-specific information may include prior 3D scan data, treatment plan data, or subjective customer feedback (e.g., customer assessment of dental aligner fit). Population-specific information may include population-level probabilities of maximum teeth movement and types of movement within a given time period.

The dental modeling computing system 100 may be configured to compare a first position of a model tooth 202 with a position of a corresponding patient tooth 402 based on the virtual camera parameter. For example, the virtual camera parameter may indicate a location of a camera with respect to the patient's dentition when the camera captured the digital representation 116. The dental modeling computing system 100 may be configured to orient the 3D model 200 with respect to a virtual camera based on the orientation of the patient's dentition with respect to the camera when the digital representation 116 was captured. For example, the digital representation 116 can include an image including the left side of the dentition and taken at the same elevation as the dentition. The dental modeling computing system 100 may orient the 3D model such that the virtual camera faces the left side of the 3D model 200 and is at the same height as the 3D model 200. The 3D model 200 may be oriented such that the portion of the patient's dentition visible in the digital representation 116 is the same portion of the 3D model that is visible by the virtual camera.

Figure 9:
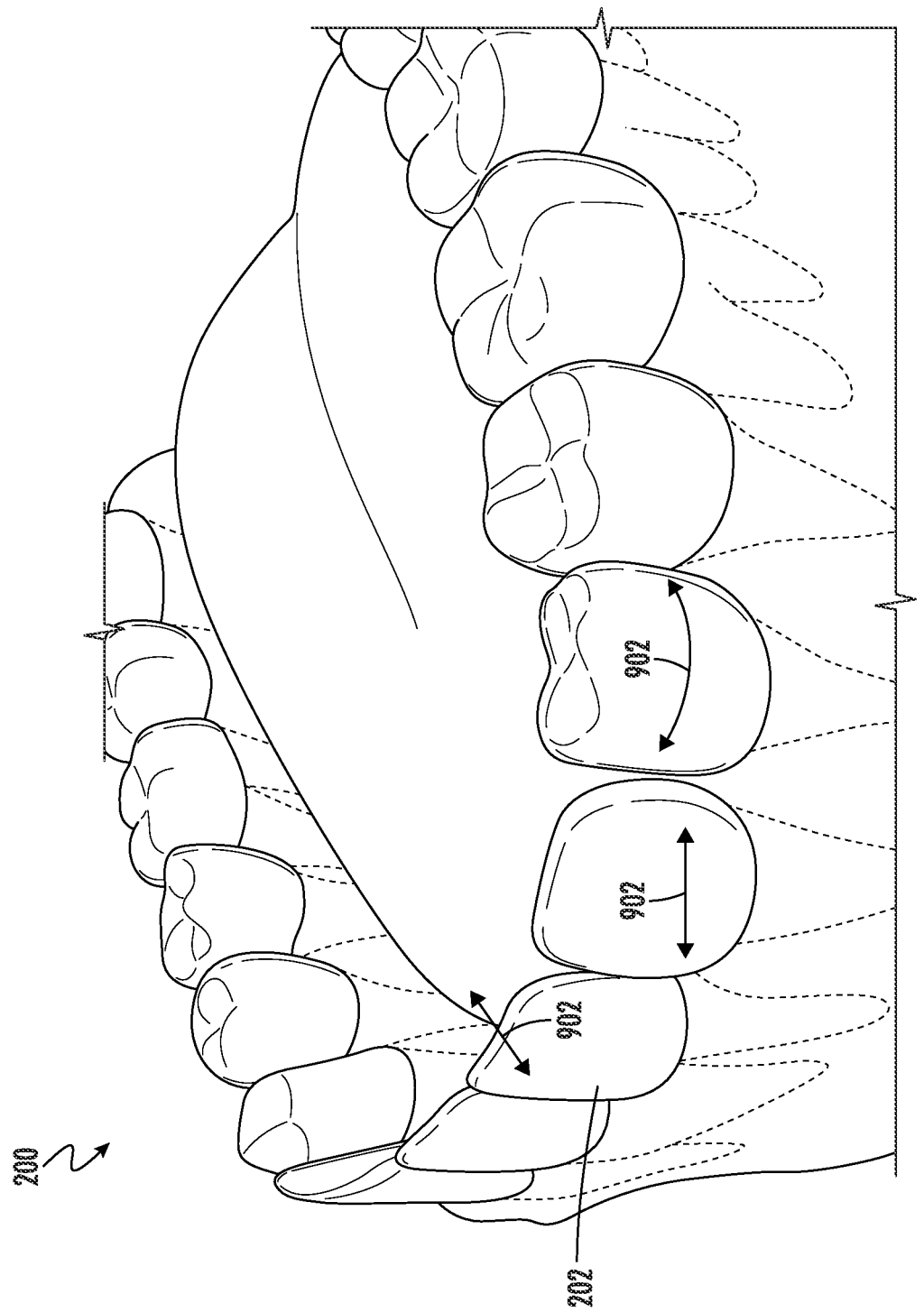
FIG. 9 shows a tooth movement of a model tooth of a 3D model, according to an illustrative embodiment.

Referring now to FIGS. 1 and 9, the dental modeling computing system 100 may be configured to determine a movement for a model tooth. For example, tooth positioning engine 112 may be configured to determine a tooth movement 902 for a model tooth 202. The tooth movement 902 may include a rotational movement, translational movement, or any combination thereof. The tooth movement 902 may be to move the model tooth 202 from a first position to a second position. The second position may be based on a position of a corresponding patient tooth 402 from at least one digital representation 116. The second position may be based on a virtual camera parameter. In some embodiments, the second position may be based on a subset of a plurality of digital representations associated with the corresponding patient tooth and the virtual camera parameter. For example, the tooth movement 902 may result in a model tooth 202 in a second position that resembles the position of the corresponding patient tooth 402 (e.g., same location, orientation, etc.). The tooth movement 902 may define translational movements and/or rotational movements. For example, based on the error metric derived from comparing the model tooth 202 of the 3D model 200 with the patient tooth 402 of the digital representation 116, the tooth positioning engine 112 may determine that to match the position of the patient tooth 402, the model tooth 202 may translate in a certain direction and rotate about a certain axis. Similarly, based on the alignment of the 3D model with the virtual camera based on the virtual camera parameter, the tooth positioning engine 112 may determine that to match the position of the patient tooth 402, the model tooth 202 may translate in a certain direction and rotate about a certain axis.

In some embodiments, the tooth positioning engine 112 may apply at least one limitation to the tooth movement 902. For example, the tooth positioning engine 112 may limit the tooth movement 902 based on a tooth movement parameter. The tooth movement parameter may restrict the model tooth 202 from moving in a certain way. The tooth movement parameter may define a range of possible tooth movements for each individual patient tooth. For example, the tooth movement parameter may define a minimum and/or maximum rotational movement the model tooth 202 may move. The boundaries of the range may be suggested boundaries (e.g., the patient tooth 402 likely did not move beyond this point) or definite boundaries (e.g., the patient tooth 402 could not have moved beyond this point). The definite boundaries may define a hard limit on the possible tooth movements of the model tooth 202 such that the model tooth 202 cannot move beyond the identified range. The suggested boundaries may be soft limits on the possible tooth movements of the model tooth 202 such that the tooth movement 902 may extend beyond the suggested boundaries. In such an embodiment, as described in more detail below, a penalty may be applied to the tooth movement 902 that extends beyond or away from the tooth movement parameter. The tooth movement parameter may be based on various factors. For example, a factor may be an adjacent structure. For example, a first model tooth 202 may be adjacent to a second model tooth 202. If there is no space between the first model tooth 202 and the second model tooth 202, the tooth movement parameter may prevent the first model tooth 202 from moving in a direction toward the second model tooth 202.

Another factor may be wear schedule data. For example, a patient tooth 402 may only move a certain distance over a certain amount of time. For example, the patient tooth 402 may only be able to move laterally 0.25 mm in one week. Therefore, if the 3D model is of a patient dentition from one week prior to when the digital representation 116 was taken, the tooth movement parameter may indicate a maximum lateral movement of 0.25 mm.

Another factor may be wear time data and/or compliance data. For example, a distance a patient tooth 402 can move may be based on the time the patient actually uses a dental appliance. For example, a patient tooth 402 may be able to move laterally 0.25 mm if a dental aligner is worn for at least 8 hours a day for 1 week (7 days). The wear time data may indicate that the patient wore the dental aligner for only 40 hours. The compliance data may indicate that the patient was only 82% compliant with the instructions. Therefore, the tooth movement parameter may indicate a maximum tooth movement of less than 0.25 mm.

Another factor may be customer feedback. For example, the customer feedback may include a discomfort level. A higher discomfort level may indicate a larger movement than a lower level of discomfort. A higher discomfort level may also indicate an undesirable movement (e.g., wrong direction). The customer feedback may also include a fit of the dental aligner. A poor fit (e.g., loose on the teeth) may indicate a lesser magnitude movement than a proper fit. A poor fit (e.g., too tight on the teeth) may also indicate a greater magnitude of movement or undesirable movement. The customer feedback may be considered alone or in combination with the wear schedule, wear time, and compliance data.

Another factor may be possible tooth movements. For example, memory 102 may include a tooth movement library. The tooth movement library may include learned possible tooth movements associated with each tooth of a dentition. The tooth positioning engine 112 may be configured to access the tooth movement library to determine the tooth movement parameter for the model tooth 202. For example, the tooth movement library may indicate that a tooth may only rotate a predetermined number of degrees, may only move in a certain direction, may only translate a predetermined amount, etc. The tooth movement parameter may include the data from the tooth movement library to define boundaries or a range of available tooth movements for the model tooth 202. The learned tooth movements may be based on clinical data, historically known movements, movements recorded in previous cases, etc. For example, the learned tooth movements may be expected movements from a treatment plan or typical movements of the teeth as evidenced by previous data. The tooth movement library may also include predicted tooth movements associated with each tooth of a dentition. For example, based on an initial position of a tooth, a second position of the tooth is predicted to move an expected amount in an expected direction. The tooth positioning engine 112 may limit available tooth movements of the model tooth 202 based on the tooth movement parameter from the tooth movement library. For example, the tooth positioning engine 112 may restrict the movement of a model tooth 202 to only the possible tooth movements in the tooth movement library. As explained in more detail below, instead of restricting certain movements, the tooth positioning engine 112 may instead apply penalties to tooth movements that deviate from the tooth movement parameter.

Determining and applying the tooth movement parameter increases the speed of determining the tooth movement by reducing the number of possible movements that the tooth can make. The tooth movement parameter also increases the accuracy of the positioning of a model tooth by eliminating or penalizing movements that are unlikely or not possible by the model tooth.

An artificial intelligence (AI) model may also be used to determine tooth movements by incorporating real tooth movements and existing data from customers. For example, the AI model may be configured to receive and analyze the actual tooth movements to learn the range of possible tooth movements and adjust the range as the AI model receives more data from more iterations. The AI model may learn to discriminate between realistic tooth movements and unrealistic tooth movements based on the actual tooth movements and may apply the realistic tooth movements to the model tooth 202 over the unrealistic tooth movements. As such, the tooth positioning engine 112 may be configured to move the model tooth 202 of the 3D model 200 based on data obtained from the AI model. In some embodiments, data obtained from the AI model may be used as a check to ensure a tooth movement determined by the tooth positioning engine 112 is realistic given a geometry of the tooth being moved or of another tooth (e.g., an adjacent tooth or a non-adjacent tooth), a prior movement of the tooth being moved or of another tooth (e.g., an adjacent tooth or a non-adjacent tooth). For example, the data obtained from the AI model may indicate a probability of a tooth moving a certain way (e.g., a magnitude, a direction, a rotation, a degree of impaction or eruption, etc.), and the tooth positioning engine 112 may determine that a determined movement of the tooth is accurate if the probability exceeds a threshold.

The tooth movement may also be determined based on receiving digital representations 116 from a patient at regular intervals. This can modify the metrics of the system specifically toward the individual patient. For example, a first patient's teeth may move faster than a second patient's teeth. If the dental modeling computing system 100 receives digital representations 116 from the first patient on a regular basis (e.g., weekly, bi-weekly, etc.) the dental modeling computing system 100 may calculate a rate of tooth movement for the first patient. The rate of tooth movement for the first patient may be different from the rate of movement from the second patient. This can personalize the results to each patient based on previously received data associated with the patient rather than data based on a sample of other patients.

In some embodiments, the tooth positioning engine 112 may establish a portion of the 3D model 200 as a reference point. The reference point may act as an anchor that has a predefined movement. For example, the predefined movement may include limited movements that the reference point may make. In some embodiments, the predefined movement is zero, such that the reference point remains stationary. A model tooth 202 moving from a first position to a second position may move relative to the reference point. The reference point may be a single point of the 3D model 200. The reference point may be a feature of the 3D model 200 (e.g., model tooth 202, gingiva, any feature of the 3D model 200). For example, the reference point may be a molar of the 3D model 200. In some embodiments, the reference point is multiple molars (e.g., a first molar and a second molar) of the 3D model 200. For example, molars may not be expected to move, so the tooth positioning engine 112 may identify the molars as the reference points and provides the molars a predefined movement of zero with respect to all translational and rotational axes (e.g., the first molar and the second molar remain stationary). In other embodiments, the tooth positioning engine 112 may provide the reference point with a predefined movement that allows some movement, but has limitations on the magnitude and direction of the movement. For example, the predefined movement may include a predicted movement of a molar (e.g., based on a treatment plan). Identifying a reference point fixes some control parameters to preset values and therefore reducing the number of variable parameters. The reference point may reduce the number of degrees of freedom in which a dentition may move (e.g., prevent the dentition from flipping upside down). The reference point may anchor the 3D model in space and prevent an infinite loop of optimization. The fewer variable parameters and the limitation of movements increases the accuracy and efficiency of moving a model tooth 202 from a first position to a second position that resembles a position of a corresponding patient tooth 402.

The tooth positioning engine 112 may be configured to move the model tooth 202 of the 3D model 200. The tooth positioning engine 112 may be configured to move the model tooth 202 according to the determined movement. The movement may identify how the model tooth 202 may move from a first position to a second position. The second position may be based on the position of the corresponding patient tooth 402 from the digital representation 116. The second position may also be based on the virtual camera parameter. Moving the model tooth 202 from the first position to the second position may include a single step. For example, the tooth positioning engine 112 may determine the movement to apply to a model tooth 202 and the tooth positioning engine 112 may apply the movement to the model tooth 202. Application of the movement to the model tooth 202 may result in the model tooth 202 being in a position that matches a tooth of the patient.

In other embodiments, moving the model tooth 202 from the first position to the second position may be an iterative process. For example, the tooth positioning engine 112 may identify at least one intermediate position. The intermediate positions may be based on different positions of a patient tooth 402 from a plurality of digital representations 116. For example, a first intermediate position may be based on a position of a patient tooth 402 from a first digital representation 116. A second intermediate position may be based on a position of the patient tooth 402 from a second digital representation 116. The second intermediate position may be a slight adjustment from the first intermediate position based on the position of the patient tooth 402 looking different in the first and second digital representations 116. In some embodiments, the intermediate positions may be based on changing a virtual camera parameter. For example, the virtual camera processing engine 110 may determine a virtual camera parameter from a first digital representation 116. The first intermediate position may be based on the virtual camera parameter. The virtual camera processing engine 110 may adjust the virtual camera parameter based on a second digital representation 116. The second intermediate position may be based on the adjusted virtual camera parameter. In some embodiments, the position of the patient tooth 402 and the virtual camera parameter may be adjusted simultaneously. In some embodiments, the iterative process may continue until the dental modeling computing system 100 reaches a stopping threshold indicating that the geometry of the patient tooth is optimized. For example, the stopping threshold may be a predetermined number of iterations. For another example, the threshold may be an algorithmic convergence. For example, a loss calculated between each iteration may become smaller and smaller such that the algorithm converges. When the algorithm reaches a predetermined loss threshold, the tooth positioning engine 112 may determine the model tooth 202 is in the second position.

The tooth positioning engine 112 may be configured to apply a penalty to a tooth movement. A penalty may indicate that the tooth movement is not satisfying, or is straying away from, a tooth movement parameter. For example, the tooth positioning engine 112 may apply a penalty to a tooth movement when the tooth movement deviates from a tooth movement parameter. The penalty may indicate to the dental modeling computing system 100 that the determined tooth movement may not accurately depict the actual position of the patient tooth 402. The dental modeling computing system 100 may use the penalty and the magnitude of the penalty to determine whether a different tooth movement is more accurate. The magnitude of the penalty may vary based on how far away the tooth movement is from the tooth movement parameter. For example, the penalty may be proportionate to the magnitude of offset of the tooth movement from the tooth movement parameter. As explained above, the tooth movement parameter may be determined by various factors including, but not limited to, adjacent structures, time lapsed, and possible tooth movements (e.g., from a tooth movement library). The tooth positioning engine 112 may be configured to apply any factor to the tooth movement and determine whether the tooth positioning engine 112 may apply a penalty to the tooth movement. For example, based on the possible tooth movements from the tooth movement library, the tooth positioning engine 112 may determine a probability of a tooth movement. If the probability is high, the tooth positioning engine 112 may apply no penalty, or a low penalty. If the probability is low, the tooth positioning engine 112 may apply a large penalty. In another example, the tooth positioning engine 112 may determine that within the time period between the patient tooth moving from a first position to a second position, the patient tooth 402 may move within a range of distances. If the tooth movement is within the range, the tooth positioning engine 112 may apply no penalty. If the tooth movement is outside the range, the tooth positioning engine 112 may apply a penalty. The penalty may grow the farther away the tooth movement is from the range.

In some embodiments, the tooth positioning engine 112 may analyze the tooth movement with respect to other structures. For example, the tooth positioning engine 112 may determine a tooth movement moves a model tooth 202 into a structure. If the structure is an adjacent model tooth 202, the tooth positioning engine 112 may determine a model tooth 202 cannot move into a space that is occupied by another model tooth 202 and apply a penalty to the tooth movement. If the structure is an obstruction identified by the digital representation processing engine 108, the tooth positioning engine 112 may determine the model tooth 202 may move into the space occupied by the obstruction and not apply a penalty to the tooth movement 902. For example, a tooth movement 902 comprising moving the model tooth 202 behind the obstruction may satisfy a tooth movement parameter. Moving behind the obstruction may not cause the tooth positioning engine 112 to generate a penalty to apply to the tooth movement 902.

Applying a penalty to a tooth movement increases the accuracy of the movement of the model tooth 202. The penalty highlights tooth movements that are not considered likely or possible. The penalty reduces or eliminates the likelihood that the model tooth 202 is moved to a position that does not accurately resemble the position of the patient tooth 402. In some embodiments, the penalty may increase as a tooth movement moves further away from a tooth movement parameter. In some embodiments, the penalty may act as a hard stop if the magnitude of the penalty reaches a predetermined threshold. For example, a tooth movement parameter may define a range of distances the patient tooth may move over a specified time period. The tooth movement parameter may not prevent the model tooth 202 from deviating (e.g., moving beyond the boundaries of the range) from the range. In such a case, a penalty may be applied to the tooth movement 902 that is outside the range. A penalty less than a predefined penalty threshold may not prevent the tooth movement 902. However, the penalty may increase the further the tooth movement 902 becomes outside the range. The penalty may prevent the model tooth 202 from undergoing the tooth movement 902 when the penalty reaches the predefined threshold. The predetermined penalty threshold may indicate a tooth movement that is unlikely or impossible for the patient tooth 402 to move, and therefore prevents the model tooth 202 from making such a movement.

Based on the tooth movement and any applied penalties, the tooth positioning engine 112 may be configured to generate a second 3D model comprising the model tooth 202 from the first 3D model in the second position. For example, the tooth positioning engine 112 may move a model tooth 202 from a first position to a second position, wherein the second position is based on a position of a corresponding patient tooth 402 from a digital representation 116. In some embodiments, the tooth positioning engine 112 may move a plurality of model teeth 202 to match a position of a plurality of corresponding patient teeth 402. The tooth positioning engine 112 may be configured to generate the second 3D model with the plurality of model teeth 202 in respective second positions. The second 3D model may not include a new mesh. For example, the second 3D model may include the same mesh of the model tooth 202 as the first 3D model, but at a different position. The second 3D model may indicate status of a patient's dentition based on the received digital representations 116. The dental modeling computing system 100 may be configured to generate the second 3D model without using a treatment plan, wherein the treatment plan defines the position (or at least the expected position) of the corresponding patient tooth 402. The dental modeling computing system 100 may determine the position of the patient tooth 402 solely from the digital representation(s) 116 received. For example, the dental modeling computing system 100 may determine the position based on a 2D image of the patient's dentition. No knowledge of the expected position of the patient tooth 402 is used.

Moving the model tooth 202 from the first position to the second position may include an iterative process. The iterative process may be done at any point of the process. For example, determining the patient tooth position may be an iterative process. For example, the digital representation processing engine 108 may determine a first position from a first digital representation 116, a second position from a second digital representation 116, and a third position from a third digital representation 116. The digital representation processing engine 108 may analyze any number of digital representations until it reaches a threshold. For example, the threshold may be a predetermined number of iterations, number of digital representations, or a plateau in a loss function. The threshold may define when the digital representation processing engine 108 has determined the accurate position of the patient tooth.

Determining the virtual camera parameter may be an iterative process. For example, the iterative process may include a plurality of virtual camera parameter adjustments. The virtual camera processing engine 110 may determine a first virtual camera parameter from a first digital representation 116, a second virtual camera parameter from a second digital representation 116, and a third virtual camera parameter from a third digital representation 116. Each virtual camera parameter may be an adjustment from a previous virtual camera parameter. The virtual camera processing engine 110 may analyze any number of digital representations until it reaches a threshold. The threshold may define when the virtual camera processing engine 110 has determined the accurate virtual camera parameter. Comparing the first position of the model tooth 202 with the position of the patient tooth 402 may be an iterative process. For example, the dental modeling computing system 100 may orient the 3D model 200 to match an orientation of a patient's dentition from a first digital representation 116 and compare the first position of the model tooth 202 with the position of the corresponding patient tooth 402 with the 3D model 200 at the first orientation and then orient the 3D model 200 to match an orientation of a patient's dentition from a second digital representation 116 and compare the first position of the model tooth 202 with the position of the corresponding patient tooth 402 with the 3D model 200 at the second orientation. The dental modeling computing system 100 may reorient the 3D model any number of times until a threshold is reached. The threshold may define when the dental modeling computing system 100 can determine an accurate second position for the model tooth 202 based on the position of the patient tooth 402.

Determining a tooth movement 902 for the model tooth 202 may be an iterative process. For example, the tooth positioning engine 112 may determine a first tooth movement 902 from a first digital representation 116 and/or virtual camera parameter, a tooth movement 902 from a second digital representation 116 and/or virtual camera parameter, and a third tooth movement 902 from a third digital representation 116 and/or virtual camera parameter. The tooth positioning engine 112 may determine movements until it reaches a threshold. Determining a tooth movement 902 may include a plurality of tooth adjustments. For example, the tooth positioning engine 112 may move the model tooth 202 based on the first tooth movement 902 and adjust the position of the model tooth 202 based on the second and third tooth movements 902. In some embodiments, the plurality of tooth adjustments and the plurality of virtual camera parameter adjustments may occur simultaneously. In some embodiments, the plurality of tooth adjustments and the plurality of virtual camera parameter adjustments may occur at different times. The tooth positioning engine 112 may determine any number of tooth movements 902 or move the model tooth 202 any number of times until it reaches a threshold. The threshold may define when the tooth positioning engine 112 has determined the accurate tooth movement 902 or the model tooth 202 is in the second position.

Figure 10:
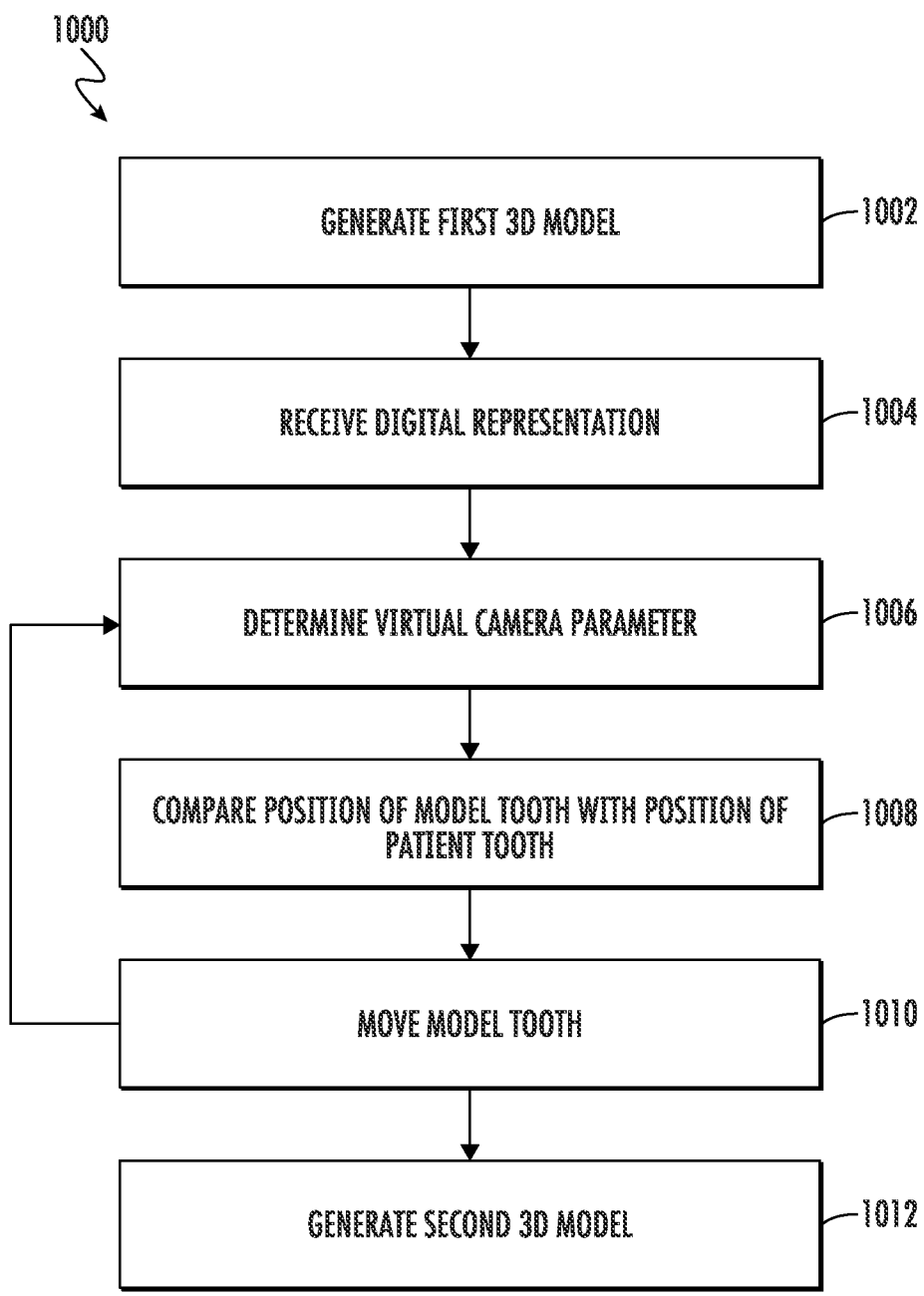
FIG. 10 shows a diagram of a method of generating a 3D model of a dentition, according to an illustrative embodiment.

Referring now to FIG. 10, a method 1000 of generating a 3D model of a dentition is shown, according to an exemplary embodiment. Method 1000 may include generating a first 3D model (step 1002), receiving a digital representation (step 1004), determining a virtual camera parameter (step 1006), comparing a position of a model tooth with a position of a patient tooth (step 1008), moving the model tooth (step 1010), and generating a second 3D model of a dentition.

At step 1002, one or more processors may generate a first 3D model (e.g., a 3D digital model). The first 3D model may represent a patient's dentition or a template dentition. To generate the first 3D model, the one or more processors may obtain data associated with the dentition. For example, model generation engine 106 of dental modeling computing system 100 may receive data from a computing system. For example, the model generation engine 106 may receive intraoral scans of a patient's dentition. The model generation engine 106 may convert the received data into the first 3D model. In another example, the one or more processors may obtain the data by retrieving data from a database. For example, the model generation engine 106 may retrieve data from memory 102. The data may include images, dimensions, scans, previously-generated models, etc. of the dentition. The model generation engine 106 may convert the retrieved data into the first 3D model. The first 3D model may include a plurality of model teeth 202. The model generation engine 106 may generate a separate mesh for each of the plurality of model teeth 202.

At step 1004, the one or more processors may receive at least one digital representation. For example, the digital representation processing engine 108 of the dental modeling computing system 100 may receive at least one digital representation 116. The digital representation processing engine 108 may receive a plurality of digital representations 116. The digital representation 116 may be, for example, a 2D image or a video. The digital representation 116 may include a plurality of patient teeth 402. The digital representation processing engine 108 may receive the at least one digital representation 116 from a user device 114. The user device 114 may be at a remote location with respect to the dental modeling computing system 100. Step 1004 may include filtering the plurality of digital representations 116. For example, the digital representation processing engine 108 may designate a subset of the plurality of digital representations 116 as useful. The dental modeling computing system 100 may use the subset of the plurality of digital representation 116 for the remaining analysis, calculations, etc. and ignore (e.g., delete, store, etc.) the remaining of the plurality of digital representations 116. Step 1004 may also include associating a subset of the plurality of digital representation 116 with a patient tooth. The associated digital representations 116 may be a subset of the filtered digital representations 116. When analyzing a patient tooth 402 from the plurality of digital representations 116, the dental modeling computing system 100 may only refer to the subset of the digital representations 116 associated with the patient tooth 402.

At step 1006, the one or more processors may determine a virtual camera parameter. The virtual camera parameter may include at least one value that is representative of a setting of a virtual camera. The virtual camera parameter may correspond with a parameter of a device (e.g., a camera of user device 114) used to capture the digital representation 116. The virtual camera parameter may include an extrinsic and/or intrinsic parameter. The extrinsic parameters may correspond with a position and/or orientation of the virtual camera. The intrinsic parameters may correspond with how the virtual camera manipulates a digital representation 116. For example, an intrinsic parameter may define at least one of a perspective or a distortion of a camera. The virtual camera processing engine 110 of the dental modeling computing system 100 may determine the virtual camera parameter. Determining the virtual camera parameter may include receiving an input indicating the virtual camera parameter or calculating the virtual camera parameter based on the digital representation(s) 116. Calculating the virtual camera parameter may include analyzing at least one digital representation 116 to identify characteristics (e.g., settings, positioning, etc.) of the device used to capture the digital representation 116. For example, calculating the virtual camera parameter may include comparing a position of a patient tooth 402 in a first digital representation 116 with a position of the patient tooth 402 in a second digital representation 116. Based on a difference between the position from the first digital representation 116 and the position from the second digital representation 116, the virtual camera processing engine 110 may determine the virtual camera parameter. The virtual camera processing engine 110 may apply any methods or algorithms, or any combination thereof, to determine a virtual camera parameter from the digital representations 116.

At step 1008, the one or more processors may compare a position of a model tooth with a position of a patient tooth. Step 1008 may include the one or more processors determining the position of the patient tooth. For example, the tooth positioning engine 112 of the dental modeling computing system 100 may identify a position of a patient tooth 402 from the digital representation(s) 116. The tooth positioning engine 112 may apply the virtual camera parameter to the digital representation 116 to identify the position of the patient tooth 402. Determining the position of the patient tooth 402 may include optimizing the geometry of the patient tooth based on the virtual camera parameters. Optimizing the geometry may include adjusting the patient tooth 402 of the digital representation 116 based on the virtual camera parameters to better resemble a realistic position of the patient's tooth. The adjustment can be made to the actual digital representation 116 or it can just be taken into account when calculating the position of the patient tooth 402. With the position of the patient tooth 402, the tooth positioning engine 112 may compare the position of the patient tooth 402 with a corresponding model tooth 202. In some embodiments, to compare the location of the model tooth 202 and the location of the corresponding patient tooth 402, model tooth 202 from the first 3D model 200 and the patient tooth 402 from the digital representation 116 are projected into an NDC space. The tooth positioning engine 112 may calculate an error metric between the location of the model tooth 202 and the corresponding patient tooth 402. The tooth positioning engine 112 may use the error metric to determine a tooth movement 902 for the model tooth 202. In some embodiments, to compare the position of the model tooth 202 and the position of the corresponding patient tooth 402, the 3D model 200 may be oriented with respect to a virtual camera based on the virtual camera parameter. The tooth positioning engine 112 may orient the 3D model 200 such that a portion of the 3D model seen by a virtual camera is the same portion of the patient's dentition that is seen by the camera that captured the digital representation 116. The tooth positioning engine 112 may determine a tooth movement 902 based on a difference between the first position of the model tooth 202 and the position of the corresponding patient tooth 402.

At step 1010, the one or more processors may move the model tooth. For example, the tooth positioning engine 112 of the dental modeling computing system 100 may move the model tooth 202. The tooth positioning engine 112 may move the model tooth 202 from a first position to a second position. The tooth positioning engine 112 may move the model tooth 202 to the second position based on the tooth movement 902. The second position and the tooth movement 902 may be based on the position of the corresponding patient tooth 402 and the virtual camera parameter. The second position is to resemble the position of the corresponding patient tooth 402 from the digital representation 116.

Steps 1006-1010 may include an iterative process. Any of the steps may repeated any number of times and in any order or combination. For example, a first virtual camera parameter value may be determined by the virtual camera processing engine 110. The first virtual camera parameter value may be used to determine the position of the patient tooth 402 from the digital representation 116. Based on the position of the patient tooth 402 and comparing the position of the patient tooth 402 with the position of the model tooth 202, the tooth positioning engine 112 may determine a first tooth movement 902 and move the model tooth 202 to an intermediate position based on the first tooth movement 902. The tooth positioning engine 112 may compare the intermediate position of the model tooth 202 with the position of the patient tooth 402. Based on the error metric identified, the virtual camera parameter may calculate a second virtual camera parameter value (or adjust the first virtual camera parameter). The process may be repeated until the position of the model tooth 202 matches (within a predetermined degree or error) the position of the patient tooth 402. The tooth positioning engine 112 may determine the position of the model tooth 202 matches the position of the patient tooth 402 by applying a threshold. For example, the threshold may include a predetermined number of iterations, a number of digital representations, or a plateau in a loss function.

At step 1012, the one or more processors may generate a second 3D model (e.g., a 3D digital model). The second 3D model may include the model tooth 202 in the second position. The second 3D model may include a plurality of model teeth 202 in respective second positions based on corresponding patient teeth 402 from the digital representation(s) 116. The one or more processors may generate the second 3D model without using a treatment plan, wherein the treatment plan defines the position (or at least the expected position) of the patient teeth 402. Generating the 3D model may not include generating a new mesh. She same mesh as the first 3D model may be used, with the individual meshes of the model teeth 202 in different positions.

Figure 11:
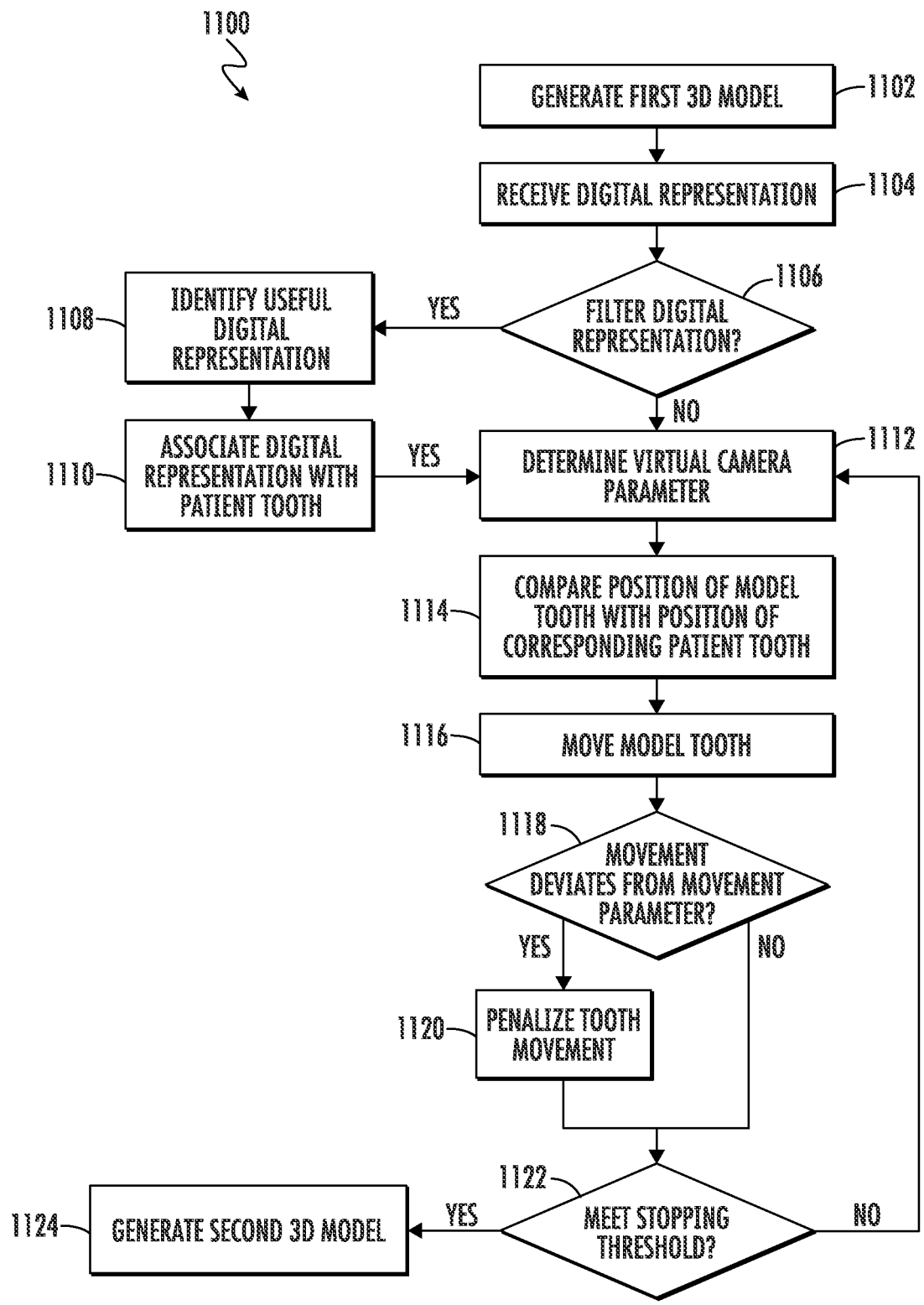
FIG. 11 shows a diagram of a method of generating a 3D model dentition, according to an illustrative embodiment.

Now referring to FIG. 11, a method 1100 of generating a 3D model of a dentition is shown, according to an exemplary embodiment. Method 1100 may include generating a first 3D model (step 1102), receiving at least one digital representation (step 1104), and determining whether to filter the at least one digital representation (step 1106). At step 1106, if the digital representations are going to be filtered, method 1100 may include identifying useful digital representations (step 1108) and associating the useful digital representations with a patient tooth (step 1110). After filtering the at least one digital representation or determining not to filter the at least one digital representation, method 1100 may include determining a virtual camera parameter (step 1112), comparing a model tooth position with a corresponding patient tooth position (step 1114), moving a model tooth from a first position to a second position (step 1116), and determining whether the tooth movement deviates from a movement parameter (step 1118). At step 1118, if the tooth movement does deviate from the movement parameter, method 1100 may include penalizing the tooth movement (step 1120). After penalizing the tooth movement or determining the tooth movement does not deviate from the movement parameter, method 1100 may include determining whether a stopping threshold is met (Step 1122). If the stopping threshold is not met, additional iterations of steps 1112-1120 in any order and any combination may be performed until the stopping threshold is met. When the stopping threshold is met, method 1100 may include generating a second 3D model (step 1124).

At step 1102, one or more processors may generate a first 3D model. Similar to step 1002, the first 3D model may include a plurality of model teeth 202. Generating the first 3D model may include obtaining data associated with a dentition. The dentition may be a patient dentition or a template dentition. At step 1104, the one or more processors may receive at least one digital representation. Similar to step 1004, the digital representation 116 may be an image, a plurality of images, a video, etc. received from a remote user device 114. In some embodiments, at step 1104, the one or more processors may receive a plurality of digital representations 116. For example, the digital representation processing engine 108 may receive a plurality of images from a user device 114. The plurality of images may include a plurality of patient teeth 402.

At step 1106, the one or more processors may determine whether to filter the at least one digital representation 116. For example, the digital representation processing engine 108 of the dental modeling computing system 100 may determine whether to filter the at least one digital representation 116. For example, when the digital representation processing engine 108 receives a single digital representation 116, the digital representation processing engine 108 may determine to not filter the digital representation 116. When the digital representation processing engine 108 receives a plurality of digital representations 116, the digital representation processing engine 108 may determine to filter the plurality of digital representations 116. In some embodiments, the digital representation processing engine 108 may determine to filter the digital representations 116 based on various factors, including but not limited to, number of digital representations received, quality of digital representations received, file size of the digital representations received, among others. For example, the digital representation processing engine 108 may determine to filter the digital representations based on a predetermined threshold number of digital representations 116 received. For example, the digital representation processing engine 108 may filter the digital representations 116 when the digital representation processing engine 108 receives ten or more digital representations 116. The digital representation processing engine 108 may filter the digital representations 116 when the digital representation processing engine 108 identifies some of the digital representations are out of focus or blurry. The digital representation processing engine 108 may filter the digital representations when the aggregate data size of the digital representations exceeds a predetermined threshold size. For example, the aggregate data size exceeds one megabyte. Filtering the digital representations 116 can reduce the storage space required to store the digital representations by removing some from the system and increase computational speed by reducing the number digital representations 116 the system analyzes to generate the second 3D model.

When the one or more processors determine to filter the digital representation 116, at step 1108, the one or more processors may identify at least one useful digital representation 116. For example, the digital representation processing engine 108 of the dental modeling computing system 100 may identify at least one useful digital representation 116. The digital representation processing engine 108 may identify a subset of a plurality of digital representations 116 that are useful. The digital representation processing engine 108 may designate a digital representation 116 as useful if the digital representation 116, for example, is in focus (e.g., not blurry, can identify details of the patient's dentition from the digital representation), includes teeth that are going to be analyzed by the dental modeling computing system 100, among others. The digital representation processing engine 108 may designate a digital representation 116 as not useful if the digital representation 116, for example, is not in focus, does not include teeth that are to be analyzed by the dental modeling computing system 100, is a duplicate of another digital representation 116 (e.g., provides substantially the same information as a different digital representation 116). Upon determination of the subset of the plurality of digital representations 116 that are useful, the digital representation processing engine 108 may ignore the remaining of the plurality of digital representations 116 that are considered not useful. For example, the digital representation processing engine 108 may delete or remove the not useful digital representation 116 from the dental modeling computing system 100. In some embodiments, the digital representation processing engine 108 may store the not useful digital representations 116 in memory 102 but only use the useful digital representations 116 for further analysis and computations.

At step 1110, the one or more processors may associate a digital representation 116 with a patient tooth. For example, the digital representation processing engine 108 of the dental modeling computing system 100 may associate a digital representation 116 with a patient tooth 402. The digital representation processing engine 108 may associate a digital representation 116 with a patient tooth 402 when the digital representation 116 includes data relevant to the patient tooth 402. For example, the digital representation processing engine 108 may associate a first digital representation 116 with a first patient tooth 402 when the first digital representation 116 includes the first patient tooth 402. The digital representation processing engine 108 may associate a second digital representation 116 with a second patient tooth 402 when the second digital representation includes the second patient tooth 402. In some embodiments, if any portion of the first patient tooth 402 is in the first digital representation 116, the digital representation processing engine 108 may associate the first digital representation 116 with the first patient tooth 402. In some embodiments, the digital representation processing engine 108 may associate the first digital representation 116 with the first patient tooth 402 if the first digital representation 116 provides enough data regarding the first patient tooth 402. For example, enough data may be determined by a predetermined portion of a patient tooth 402 being visible in the digital representation 116. For example, the digital representation processing engine 108 may associate the first digital representation 116 with the first patient tooth 402 if at least 50% of the front surface of the first patient tooth 402 is shown.

In some embodiments, a digital representation 116 may be associated with a plurality of patient teeth 402. For example, when the first digital representation 116 includes both a first patient tooth 402 and a second patient tooth 402, the digital representation processing engine 108 may associate the first digital representation 116 with both the first patient tooth 402 and the second patient tooth 402. A digital representation 116 may be associated with any number of patient teeth 402.

The digital representation processing engine 108 may associate a digital representation 116 with a patient tooth with or without a subset of a plurality of digital representations 116 being identified as useful at step 1108. For example, the digital representation processing engine 108 may associate all received digital representations 116 with at least one patient tooth 402 or may associate only the subset of the plurality of digital representations 116 with at least one patient tooth 402. In some embodiments, the digital representation processing engine 108 may only associate a threshold number of digital representations 116 with a patient tooth 402. For example, the digital representation processing engine 108 may limit the number of digital representations 116 that may be associated with a single patient tooth 402. The digital representation processing engine 108 may determine which set of digital representations 116 provide the most information regarding the position of the patient tooth 402, and associate that set of digital representations 116 with the patient tooth 402. Associating digital representations 116 with a specific patient tooth 402 reduces the computational strain on the system by reducing the volume of data being analyzed for a specific patient tooth 402. Associating digital representations with the specific tooth also increases the efficiency and accuracy of the system by only analyzing digital representations 116 that provide relevant data regarding the specific patient tooth 402. Limiting the number of associations further reduces the computational strain and increases the efficiency and accuracy of the system.

At step 1112, the one or more processors may determine a virtual camera parameter. For example, the virtual camera processing engine 110 of the dental modeling computing system 100 may determine a virtual camera parameter. The virtual camera parameter may include at least one value that is representative of a setting of a virtual camera. The virtual camera parameter may correspond with a parameter of a device (e.g., a camera of user device 114) used to capture the digital representation 116. The virtual camera parameter may include an extrinsic and/or intrinsic parameter. The extrinsic parameters may correspond with a position and/or orientation of the virtual camera. The intrinsic parameters may correspond with how the virtual camera manipulates a digital representation 116. For example, an intrinsic parameter may define at least one of a perspective or a distortion of a camera. Determining the virtual camera parameter may include receiving an input indicating the virtual camera parameter or calculating the virtual camera parameter based on the digital representation(s) 116. Calculating the virtual camera parameter may include analyzing at least one digital representation 116 to identify characteristics (e.g., settings, positioning, etc.) of the device used to capture the digital representation 116. The virtual camera processing engine 110 may apply any methods or algorithms, or any combination thereof, to determine a virtual camera parameter from the digital representations 116.

At step 1114, the one or more processing engines may compare a position of a model tooth with a positon of a patient tooth. Step 1114 may include the one or more processors determining the position of the patient tooth. With the position of the patient tooth 402, the tooth positioning engine 112 may compare the position of the patient tooth 402 with a corresponding model tooth 202. In some embodiments, to compare the location of the model tooth 202 and the location of the corresponding patient tooth 402, model tooth 202 from the first 3D model 200 and the patient tooth 402 from the digital representation 116 are projected into an NDC space. The tooth positioning engine 112 may calculate an error metric between the location of the model tooth 202 and the corresponding patient tooth 402. The tooth positioning engine 112 may use the error metric to determine a tooth movement 902 for the model tooth 202. In some embodiments, to compare the location of the model tooth 202 and the location of the corresponding patient tooth 402, the 3D model 200 may be oriented with a virtual camera based on the virtual camera parameter. The tooth positioning engine 112 may orient the 3D model 200 such that a portion of the 3D model seen by a virtual camera is the same portion of the patient's dentition that is seen by the camera that captured the digital representation 116. The tooth positioning engine 112 may determine a tooth movement 902 based on a difference between the first position of the model tooth 202 and the position of the corresponding patient tooth 402.

At step 1116, the one or more processors may move the model tooth. For example, the tooth positioning engine 112 of the dental modeling computing system 100 may move the model tooth 202. The tooth positioning engine 112 may move the model tooth 202 from a first position to a second position. The tooth positioning engine 112 may move the model tooth 202 to the second position based on the tooth movement 902. The second position and the tooth movement 902 may be based on the position of the corresponding patient tooth 402 and the virtual camera parameter. The second position is to resemble the position of the corresponding patient tooth 402 from the digital representation 116.

At step 1118, the one or more processors may determine whether the tooth movement deviates from a tooth movement parameter. For example, tooth positioning engine 112 of the dental modeling computing system 100 may determine whether the tooth movement deviates from a movement parameter. Step 1118 may include the one or more processors determining the tooth movement parameter. For example, the tooth positioning engine 112 may determine the tooth movement parameter. The tooth movement parameter may restrict the model tooth 202 from moving in a certain way. The tooth movement parameter may define a range of possible tooth movements for each individual patient tooth. For example, the tooth movement parameter may define a minimum and/or maximum rotational movement the model tooth 202 may move. The boundaries of the range may be suggested boundaries (e.g., the patient tooth 402 likely did not move beyond this point) or definite boundaries (e.g., the patient tooth 402 could not have moved beyond this point). The tooth positioning engine 112 may determine the tooth movement parameter by, for example, accessing a tooth movement library from memory 102, identifying structures adjacent to the model tooth 202, applying a treatment plan associated with the patient, or any combination thereof.

To determine whether the tooth movement deviates from the tooth movement parameter, the tooth positioning engine 112 may compare the actual tooth movement with the boundaries defined by the tooth movement parameter. When the tooth movement exceeds or is outside of the boundaries, the tooth movement may deviate from the tooth movement parameter. When the tooth movement remains within the boundaries, the tooth movement may not deviate from the tooth movement parameter.

When the one or more processors determine the tooth movement does deviate from the tooth movement parameter, at step 1120, the one or more processors may penalize the tooth movement. For example, the tooth positioning engine 112 of the dental modeling computing system 100 may apply a penalty to the tooth movement. The penalty may indicate to the dental modeling computing system 100 that the tooth movement may not be an accurate representation of the patient tooth 402. Therefore, when the dental modeling computing system 100 analyzes other digital representations or is solving for other virtual camera parameters, the dental modeling computing system 100 may determine values and movements that reduce the penalty on the tooth movement may be more accurate than values and movements that increase the penalty.

Applying the penalty may include preventing a tooth movement. For example, the tooth positioning engine 112 may apply a penalty threshold. If a tooth movement reaches the penalty threshold, the tooth positioning engine 112 may restrict the model tooth 202 from moving any further in the direction of the current tooth movement. In some embodiments, any penalty may prevent a tooth movement if the boundaries defined by the tooth movement parameter are definite boundaries. For example, a definite boundary may define a tooth movement that is likely impossible (e.g., flipping a tooth upside down). In such a case, the tooth positioning engine 112 may prevent the tooth movement and prevent the model tooth 202 from flipping upside down.

At step 1122, the one or more processors may determine whether a stopping threshold is met. In some embodiments, steps 1112-1122 may include an iterative process. For example, steps 1112-1122 may be performed any number of times, in any combination, and in any order. Determining whether a stopping threshold is met may include determining when the iterative process may end. For example, the stopping threshold may be a predetermined number of iterations. For another example, the threshold may be an algorithmic convergence. For example, a loss calculated between each iteration may become smaller and smaller such that the algorithm converges. When the algorithm reaches a predetermined loss threshold, the tooth positioning engine 112 may determine the model tooth 202 is in the second position. The stopping threshold may define when the model tooth 202 is in the second position that accurately resembles the position of the corresponding patient tooth 402.

At step 124, the one or more processors may generate a second 3D model. The second 3D model may include the model tooth 202 in the second position. In some embodiments, the second 3D model includes a plurality of model teeth 202, each in a respective second position. The second 3D model may resemble the patient's dentition from the digital representations 116 received. Generating the second 3D model may not include generating a new 3D mesh. The second 3D model may include the 3D mesh from the first 3D model, with the mesh of the individual model teeth 202 oriented with the model teeth 202 in the second position.

The embodiments described herein have been described with reference to drawings. The drawings illustrate certain details of specific embodiments that provide the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As utilized herein, terms of degree such as "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to any precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that terms such as "exemplary," "example," and similar terms, as used herein to describe various embodiments, are intended to indicate that such embodiments are possible examples, representations, or illustrations of possible embodiments, and such terms are not intended to connote that such embodiments are necessarily extraordinary or superlative examples.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any element on its own or any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the drawings. It should be noted that the orientation of various elements may differ according to other exemplary embodiments, and that such variations are intended to be encompassed by the present disclosure.

As used herein, the term "engine" may include hardware and machine-readable media storing instructions thereon for configuring the hardware to execute the functions described herein. The engine may be embodied as one or more circuitry components including, but not limited to, processing circuitry, network interfaces, peripheral devices, input devices, output devices, sensors, etc. In some embodiments, the engine may take the form of one or more analog circuits, electronic circuits (e.g., integrated circuits (IC), discrete circuits, system on a chip (SOCs) circuits, etc.), telecommunication circuits, hybrid circuits, and any other type of circuit. In this regard, the engine may include any type of component for accomplishing or facilitating achievement of the operations described herein. For example, an engine as described herein may include one or more transistors, logic gates (e.g., NAND, AND, NOR, OR, XOR, NOT, XNOR, etc.), resistors, multiplexers, registers, capacitors, inductors, diodes, wiring, and so on).

An engine may be embodied as one or more processing circuits comprising one or more processors communicatively coupled to one or more memory or memory devices. In this regard, the one or more processors may execute instructions stored in the memory or may execute instructions otherwise accessible to the one or more processors. The one or more processors may be constructed in a manner sufficient to perform at least the operations described herein. In some embodiments, the one or more processors may be shared by multiple engines (e.g., engine A and engine B may comprise or otherwise share the same processor which, in some example embodiments, may execute instructions stored, or otherwise accessed, via different areas of memory).

Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be provided as one or more suitable processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given engine or components thereof may be disposed locally (e.g., as part of a local server, a local computing system, etc.) or remotely (e.g., as part of a remote server such as a cloud based server). To that end, engines as described herein may include components that are distributed across one or more locations.

An example system for providing the overall system or portions of the embodiments described herein might include one or more computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

Although the drawings may show and the description may describe a specific order and composition of method steps, the order of such steps may differ from what is depicted and described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions, and arrangement of the embodiments without departing from the scope of the present disclosure as expressed in the appended claims.

What is claimed is:

1. A method comprising:
generating, by one or more processors, a first 3D model of a dentition, the dentition comprising a plurality of model teeth;
receiving, by the one or more processors, at least one digital representation comprising a plurality of patient teeth, the at least one digital representation comprising at least one of a 2D image or a video;
determining, by the one or more processors, a virtual camera parameter associated with a virtual camera, wherein the virtual camera parameter corresponds with a parameter of a camera used to capture the at least one digital representation;
comparing, by the one or more processors based on the virtual camera parameter, a first position of a model tooth of the first 3D model with a position of a corresponding patient tooth of the at least one digital representation;
moving, by the one or more processors, the model tooth of the first 3D model from the first position to a second position, wherein the second position is based on the actual relative 3D position of the corresponding patient tooth, and moving the model tooth from the first position to the second position comprises an iterative process, the iterative process comprising a plurality of tooth adjustments and a corresponding plurality of virtual camera parameter adjustments made respective to the at least one digital representation; and generating, by the one or more processors, a second 3D model comprising the model tooth of the first 3D model in the second position.

2. The method of claim 1, wherein the virtual camera parameter comprises an extrinsic parameter, the extrinsic parameter defining at least one of a translational matrix or a rotational matrix of the camera.

3. The method of claim 1, wherein the virtual camera parameter comprises an intrinsic parameter, the intrinsic parameter defining at least one of a perspective or a distortion of the camera.

4. The method of claim 1, further comprising establishing a reference point of the 3D model, wherein the model tooth of the first 3D model moves relative to the reference point, the reference point comprising a predefined movement.

5. The method of claim 4, wherein the reference point comprises a first molar or a second molar of the 3D model, wherein the predefined movement of the first molar or the second molar comprises remaining stationary.

6. The method of claim 1, further comprising:
receiving, by the one or more processors, a plurality of digital representations, wherein the plurality of digital representations comprise at least one of a plurality of individually captured images or the video;
identifying, by the one or more processors, a subset of the plurality of digital representations, wherein each of the subset of the plurality of digital representations comprises a predetermined portion of the corresponding patient tooth; and
associating, by the one or more processors, the subset of the plurality of digital representations with the corresponding patient tooth;
wherein the second position of the model tooth is based on the subset of the plurality of digital representations associated with the corresponding patient tooth and the virtual camera parameter.

7. The method of claim 1, further comprising:
limiting, by the one or more processors, a tooth movement based on a tooth movement parameter; and
applying, by the one or more processors, a penalty to the tooth movement when the tooth movement deviates from the tooth movement parameter.

8. The method of claim 7, wherein the tooth movement parameter defines a range of possible tooth movements.

9. The method of claim 7, further comprising:
accessing, by the one or more processors, a tooth movement library to determine the tooth movement parameter for the model tooth of the first 3D model; and
limiting, by the one or more processors, available tooth movements of the model tooth of the first 3D model based on the tooth movement parameter from the tooth movement library.

10. The method of claim 7, wherein the penalty prevents the model tooth from undergoing a possible tooth movement based on the penalty reaching a predefined threshold.

11. The method of claim 7, further comprising:
designating, by the one or more processors, a feature in the at least one digital representation as an obstruction, wherein the tooth movement comprising moving the model tooth behind the obstruction satisfies the tooth movement parameter.

12. The method of claim 1, further comprising applying, by the one or more processors, a threshold to the iterative process, the threshold defining when the model tooth is in the second position within a threshold degree of accuracy.

13. The method of claim 12, wherein the threshold comprises at least one of a fixed number of iterations or a plateau in a loss function.

14. The method of claim 1, wherein the one or more processors do not use a treatment plan to generate the second 3D model with the model tooth in the second position, wherein the treatment plan defines an expected position of the corresponding patient tooth.

15. The method of claim 1, further comprising:
modifying a geometry of the corresponding patient tooth of the at least one digital representation based on the virtual camera parameter;
wherein the comparison of the first position of the model tooth of the first 3D model with the position of the corresponding patient tooth of the at least one digital representation is based on the modified geometry of the corresponding patient tooth of the at least one digital representation.

16. The method of claim 1, wherein the plurality of model teeth are based on a shape of template teeth from a template model dentition.

17. A system comprising:
a processor; and
a memory coupled with the processor, wherein the memory is configured to store instructions that, when executed by the processor, cause the processor to:
generate a first 3D model of a dentition, the dentition comprising a plurality of model teeth;
receive at least one digital representation comprising a plurality of patient teeth, the at least one digital representation comprising at least one of a 2D image or a video;
determine a virtual camera parameter associated with a virtual camera, wherein the virtual camera parameter corresponds with a parameter of a camera used to capture the at least one digital representation;
compare, based on the virtual camera parameter, a first position of a model tooth of the first 3D model with a position of a corresponding patient tooth of the at least one digital representation;
move the model tooth of the first 3D model from the first position to a second position, the second position based on the position of the corresponding patient tooth, wherein moving the model tooth from the first position to the second position comprises an iterative process, the iterative process comprising a plurality of tooth adjustments and a corresponding plurality of virtual camera parameter adjustments made respective to the at least one digital representation; and
generate a second 3D model comprising the model tooth of the first 3D model in the second position.

18. The system of claim 17, wherein the instructions, when executed by the processor, further cause the processor to:
receive a plurality of digital representations, wherein the plurality of digital representations comprise at least one of a plurality of individually captured images or the video;
identify a subset of the plurality of digital representations, wherein each of the subset of the plurality of digital representations comprises a predetermined portion of the corresponding patient tooth; and associate the subset of the plurality of digital representations with the corresponding patient tooth;

wherein the second position of the model tooth is based on the subset of the plurality of digital representations associated with the corresponding patient tooth and the virtual camera parameter.

19. A non-transitory computer readable medium storing instructions that, when executed by one or more processors, cause the one or more processors to:

generate a first 3D model of a dentition, the dentition comprising a plurality of model teeth;

receive at least one digital representation comprising a plurality of patient teeth, the at least one digital representation comprising at least one of a 2D image or a video;

determine a virtual camera parameter associated with a virtual camera, wherein the virtual camera parameter corresponds with a parameter of a camera used to capture the at least one digital representation;

compare, based on the virtual camera parameter, a first position of a model tooth of the first 3D model with a position of a corresponding patient tooth of the at least one digital representation;

move the model tooth of the first 3D model from the first position to a second position, the second position based on the position of the corresponding patient tooth, wherein moving the model tooth from the first position to the second position comprises an iterative process, the iterative process comprising a plurality of tooth adjustments and a corresponding plurality of virtual camera parameter adjustments made respective to the at least one digital representation; and generate a second 3D model comprising the model tooth of the first 3D model in the second position.

* * * * *